US010428385B2

(12) United States Patent
Grönberg et al.

(10) Patent No.: US 10,428,385 B2
(45) Date of Patent: Oct. 1, 2019

(54) PROGNOSTIC METHOD FOR INDIVIDUALS WITH PROSTATE CANCER

(71) Applicant: Phadia AB, Uppsala (SE)

(72) Inventors: Henrik Grönberg, Umeå (SE); Martin Eklund, Stockholm (SE)

(73) Assignee: PHADIA AB, Uppsala (SE)

( * ) Notice: Subject to any disclaimer, the term of this patent is extended or adjusted under 35 U.S.C. 154(b) by 563 days.

(21) Appl. No.: 14/443,974

(22) PCT Filed: Nov. 20, 2013

(86) PCT No.: PCT/EP2013/074270
§ 371 (c)(1),
(2) Date: May 19, 2015

(87) PCT Pub. No.: WO2014/079874
PCT Pub. Date: May 30, 2014

(65) Prior Publication Data
US 2015/0284804 A1 Oct. 8, 2015

(30) Foreign Application Priority Data

Nov. 20, 2012 (SE) ..................... 1251310
May 16, 2013 (SE) ..................... 1350602

(51) Int. Cl.
C12Q 1/68 (2018.01)
G01N 33/53 (2006.01)
C12Q 1/6886 (2018.01)
G16B 40/00 (2019.01)

(52) U.S. Cl.
CPC ........... *C12Q 1/6886* (2013.01); *G16B 40/00* (2019.02); *C12Q 2600/118* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

2012/0150032 A1* 6/2012 Gudmundsson ..... C12Q 1/6886
600/437
2012/0202888 A1 8/2012 Ma
2015/0094221 A1 4/2015 Gronberg et al.
2015/0317431 A1 11/2015 Grönberg et al.

FOREIGN PATENT DOCUMENTS

WO 2008096375 A2 8/2008
WO 2012/031207 A2 3/2012
WO 2013/172779 A2 11/2013
WO 2014/079865 A1 5/2014

OTHER PUBLICATIONS

Handbook of Chemistry and Physics, 49th Edition, 1968, Weast (ed.), The Chemical Rubber Co., Cleveland, Ohio, p. A-245.*
Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Official Action from corresponding European Application No. 13799501.5, dated Oct. 11, 2016.
Anders Bjartell, Genetic Markers and the Risk of Developing Prostate Cancer, European Urology, 60:29-31 (Jan. 1, 2011).
Vickers et al., Reducing Unnecessary Biopsy During Prostate Cancer Screening Using a Four-Kallikrein Panel: An Independent Replication, Journal of Clinical Oncology, vol. 28, No. 15, pp. 2493-2498 (May 20, 2010).
Johansson et al., Combining 33 genetic variants with prostate-specific antigen for prediction of prostate cancer: longitudinal study, International Journal of Cancer, 130:129-137 (online: Feb. 15, 2011).
Klein et al., Evaluation of Multiple Risk-Associated Single Nucleotide Polymorphisms Versus Prostate-Specific Antigen at Baseline to Predict Prostate Cancer in Unscreened Men, European Urology, 61:471-477 (online: Nov. 9, 2011).
Official Action from European Application No. 13727408.0, dated Feb. 24, 2016.
Official Action from European Application No. 13792689.5, dated Mar. 21, 2016.

(Continued)

Primary Examiner — James Martinell
(74) Attorney, Agent, or Firm — Porter Wright Morris & Arthur LLP

(57) ABSTRACT

The present invention relates generally to the detection and identification of various forms of genetic markers, and various forms of proteins, which have the potential utility as diagnostic markers. By determining the level of a plurality of biomarkers and genetic markers in a patient sample, and combining the obtained values according to a predefined formula, it is possible to forecast if it is likely that the prostate cancer patient will require active therapy like radiation therapy or surgery. A method based on a redundantly designed combination of data is disclosed for estimating if prostate cancer is aggressive or indolent. Said method combines SNP data to form a composite value, wherein at least 5% of the SNPs can be disregarded.

19 Claims, 2 Drawing Sheets

(56) References Cited

OTHER PUBLICATIONS

Nordstrom et al., A Genetic Score Can Identify Men at High Risk for Prostate Cancer Among Men With Prostate-Specific Antigen of 1-3 ng/ml, European Urology, 65:1184-1190 (2014, online Jul. 19, 2013).

Nordstrom et al., Comparison Between the Four-kallikrein Panel and Prostate Health Index for Predicting Prostate Cancer, European Urology, 68:139-146 (2015, online Jul. 1, 2015).

Aly et al., Polygenic Risk Score Improves Prostate Cancer Risk Prediction: Results from the Stockholm-1 Cohort Study, European Urology, 60:21-28 (2011).

Collette et al., Prostate Specific Antigen: A Prognostic Marker of Survival in Good Prognosis Metastatic Prostate Cancer? (EORTC 30892), European Urology, 44:182-189 (2003).

Klein et al., Blood Biomarker Levels to Aid Discovery of Cancer-Related Single-Nucleotide Polymorphisms: Kallikreins and Prostate Cancer, Cancer Prev Res, 3(5):611-619 (2010).

Shiiki et al., Association between saliva PSA and serum PSA in conditions with prostate adenocarcinoma, Biomarkers, 16(6):498-503 (2011).

Ewing et al., Germline Mutations in HOXB13 and Prostate-Cancer Risk, The New England Journal of Medicine, 366 (2):141-9 (2012).

Cybulski et al., A Novel Founder CHEK2 Mutation is Associated with Increased Prostate Cancer Risk, Cancer Res, 64:2677-2679 (2004).

Cybulski et al., NBS1 Is a Prostate Cancer Susceptibility Gene, Cancer Res, 64:1215-1219 (2004).

Magi et al., Contribution of 32 GWAS-Identified Common Variants to Severe Obesity in European Adults Referred for Bariatric Surgery, PLOS One, vol. 8, Issue 8: 1-9 (Aug. 2013).

Song et al., Whole Milk Intake Is Associated with Prostate Cancer-Specific Mortality among U.S. Male Physicians 1-4, The Journal of Nutrition, 143:189-196 (2013, online Dec. 19, 2012).

Hastie et al., The Elements of Statistical Learning, Data Mining, Inference, and Prediction, Springer Series in Statistics, Second Edition (Aug. 2008), pp. vii-xxii only.

Brown et al., Macrophage Inhibitory Cytokine1: A New Prognostic Marker in Prostate Cancer, Clin Cancer Res, 15 (21) (2009).

Johnson et al., Genome-Wide Association Scan Identifies a Risk Locus for Preeclampsia on 2q14, Near the Inhibin, Beta B. Gene, Plos One, vol. 7, No. 3, p. 1-11 (Mar. 14, 2012).

Kader et al., Potential Impact of Adding Genetic Markers to Clinical Parameters in Predicting Prostate Biopsy Outcomes in Men Following an Initial Negative Biopsy: Findings from the Reduce Trial, European Urology, 62 (6):953-961 (online May 11, 2012).

Xu et al., Inherited genetic variant predisposes to aggressive but not indolent prostate cancer, Proceedings of the National Academy of Sciences, vol. 107, No. 5, pp. 2136-2140 (Feb. 2, 2010).

Amin Al Olama et al., A meta-analysis of genome-wide association studies to identify prostate cancer suspectibility loci associated with aggressive and non-aggressive disease, Human Molecular Genetics, vol. 22, No. 2, pp. 408-415 (Oct. 12, 2012).

Jin et al., Genome-wide copy-number variation analysis identifies common genetic variants at 20p13 associated with aggressiveness of prostate cancer, Carcinogenisis, vol. 32, No. 7, pp. 1057-1062 (May 5, 2011).

Choudhury et al., The Role of Genetic Markers in the Management of Prostate Cancer, European Urology, 62 (4):577-587 (online Jun. 5, 2012).

Nordstrom et al., Prostate-specific Antigen (PSA) Testing Is Prevalent and Increasing in Stockholm County, Sweden, Despite No Recommendations for PSA Screening: Results from a Population-based Study, 2003-2011, European Association of Urology, 63:419-425 (online Oct. 12, 2012).

Olama A., Kote-Jarai et al., A meta-analysis of genome-wide association studies to identify prostate cancer susceptibility loci associated with aggressive and non-aggressive disease, Human Molecular Genetics, vol. 22, No. 2., pp. 408-415 (published Oct. 12, 2012).

Official Action dated Oct. 31, 2017 from corresponding Russian Patent Application No. 2015124008, and English Translation.

Jin et al., Genome-wide copy-number variation analysis identifies common genetic variants at 20p13 associated with aggressiveness of prostate cancer, vol. 32, No. 7, pp. 1057-1062 (May 5, 2011).

Breyer et al., Confirmation of the HOXB13 G84E Germline Mutation in Familial Prostate Cancer, Cancer Epidemiol Biomarkers Prev., 21(8):1348-1353 (Aug. 2012).

Lindstrom et al., Characterizing Associations and SNP-Environment Interactions for GWAS-Identified Prostate Cancer Risk Markers—Results from BPC3, PLoS One, vol. 6, Issue 2E17142, pp. 1-11 (Feb. 2011).

Haiman et al., Genome-wide association study of prostate cancer in men of African ancestry identifies a susceptability locus at 17q21, Nat Genet., 43(6):570-573 (Jun. 2011).

Vickers et al., A panel of kallikrein markers can reduce unnecessary biopsy for prostate cancer. data from the European Randomized Study of Prostate Cancer Screening in Goteborg, Sweden, BMC Medicine, 6:19, pp. 1-10 (2008).

Ramirez et al., Beyond prostate-specific antigen: alternate serum markers, Prostate Cancer and Prostalic Diseases, 11:216-229 (2008).

Eeles et al., Identification of 23 new prostate cancer susceptibility loci using the iCOGS custom genotyping array, Nat Genet., 45(4):385-91 (Apr. 2013).

Sung Kyu Hong, Kallikreins as Biomarkers for Prostate Cancer, BioMed Research International, vol. 2014 ID 526341, pp. 1-10 (2014).

Kote-Jarai et al., Seven novel prostate cancer susceptibility loci identified by a multi-stage genome-wide association study, Nat Genet., vol. 43, No. 8, pp. 785-791 (2011).

Gudmundsson et al., Genome-wide association and replication studies identify four variants associated with prostate cancer susceptibility, Nat Genet., 41(10):1122-1126 (Oct. 2009).

Gudmundsson et al., Genetic correction of PSA values using sequence variants associated with PSA levels, Sci Transl Med., 2(62):62ra92 (Dec. 15, 2010).

Lindstrom et al., Replication of five prostate cancer loci identified in an Asian population—Results from the NCI Breast and Prostate Cancer Cohort Consortium (BPC3), Cancer Epidemiol Biomarkers Prev. 21(1):212-216 (Jan. 2012).

Schumacher et al., Genome-wide association study identifies new prostate cancer susceptibility loci, Human Molecular Genetics, vol. 20, No. 19, pp. 3867-3875 (Jul. 8, 2011).

Official Action dated Oct. 24, 2017 from corresponding Japanese Patent Application No. 2015-542310 with English Translation.

Invitation to Oral Proceedings dated Jun. 2, 2017 from corresponding European Patent Application No. 13799501.5.

Bjartell, Anders, Genetic Markers and the Risk of Developing Prostate Cancer, European Urology, vol. 60, pp. 29-31 (2011).

Klein, Robert J. et al., Evaluation of Multiple Risk-Associated Single Nucleotide Polymorphisms Versus Prostate-Specific Antigen at Baseline to Predict Prostate Cancer in Unscreened Men, European Urology, vol. 61, No. 3, pp. 471-477 (2011).

English Translation of Official Action dated 2018 from corresponding Russian application No. 2015124008.

Johnson et al., Genome-Wide Association Scan Identifies a Risk Locus for Preeclampsia on 2q14, Near the Inhibin, Beta B Gene, vol. 7, Issue 3, pp. 1-11 (Mar. 2012).

Examination report No. 1 for standard patent application dated Oct. 4, 2018 to corresponding Australian Application No. 2013349721.

* cited by examiner

PROGNOSTIC METHOD FOR INDIVIDUALS WITH PROSTATE CANCER

FIELD OF THE INVENTION

The present invention relates generally to the detection and identification of various forms of genetic markers, and various forms of proteins, which have the potential utility as prognostic markers. In particular, the present invention relates to the simultaneous use of multiple prognostic markers for improved estimation of whether an individual having prostate cancer will require treatment of the prostate cancer in the future.

BACKGROUND OF THE INVENTION

The measurement of serum prostate specific antigen (PSA) is widely used for the screening and early detection of prostate cancer (PCa). As discussed in the public report "Polygenic Risk Score Improves Prostate Cancer Risk Prediction: Results from the Stockholm-1 Cohort Study" by Markus Aly and co-authors as published in EUROPEAN UROLOGY 6 0 (2011) 21-28 (which is incorporated by reference herein), serum PSA that is measurable by current clinical immunoassays exists primarily as either the free "non-complexed" form (free PSA), or as a complex with a-lantichymotrypsin (ACT). The ratio of free to total PSA in serum has been demonstrated to significantly improve the detection of PCa. Other factors, like age and documented family history may also improve the detection of PCa further. The measurement of genetic markers related to PCa, in particular single nucleotide polymorphisms (SNP), is an emerging modality for the screening and early detection of prostate cancer. Analysis of multiple PCa related SNPs can, in combination with biomarkers like PSA and with general information about the patient improve the risk assessment through a combination of several SNPs into a genetic score.

Attempts to combine information from multiple sources into one algorithmic model have been disclosed in the past for the prediction of a different end-point, PCa risk, as compared to the present invention. In the public report "Blood Biomarker Levels to Aid Discovery of Cancer-Related Single-Nucleotide Polymorphisms: Kallikreins and Prostate Cancer" by Robert Klein and co-authors as published in Cancer Prev Res (2010), 3(5):611-619 (which is incorporated by reference herein), the authors discuss how blood biomarkers can aid the discovery of novel SNP, but also suggest that there is a potential role for incorporating both genotype and marker levels in predictive models for the estimation of PCa risk. Furthermore, this report provides evidence that the non-additive combination of genetic markers and biomarkers in concert may have predictive value for the estimation of PCa risk. Later, Xu and co-inventors disclosed a method for assessing the risk of a subject having PCa in the patent application WO2012/031207A2, which is incorporated by reference herein. This disclosure describes a method to predict if an individual is at risk of having prostate cancer through the use of genetic information in 33 defined SNP, which implicitly can be used for the prediction of if the tested individual is suitable for chemopreventive therapy. Chemopreventive therapy is proactive medication supplied prior to cancer diagnosis, with the purpose of reducing the likelihood of cancer onset.

Even though PSA is predominantly used for diagnosis of PCa, it has also been described as a prognostic marker for individuals that are diagnosed with PCa. One possible method for estimating the prognosis of PCa in an individual is to follow the progression of the PSA value, as described by Collette and co-authors in the public report "Prostate specific antigen: a prognostic marker of survival in good prognosis metastatic prostate cancer?" as published in Eur Urol. 2003 August; 44(2):182-9; discussion 189 (which is incorporated by reference herein).

There are further other markers suitable for assessing the prognosis of a PCa diagnosis, as described by EP Gelmann and SM Henshall in the public report "Clinically Relevant Prognostic Markers for Prostate Cancer: The Search Goes On" as published in Ann Intern Med. 5 May 2009; 150(9): 647-649 (which is incorporated by reference herein). In this report, the histologic grade (Gleason score), P53 expression, BCL2 expression and microvessel density are discussed as potential prognostic markers, even though they all have major shortcomings for that purpose.

The current clinical practice (in Sweden) is to use the Gleason score as one major input for decision on if to engage in active treatment (surgery or radiation therapy) for prostate cancer that is confined to the prostate gland. Other factors, like age, unrelated diseases, estimated tumor extent, and the opinion of the patient are also important for this decision. As a rule of thumb, the vast majority of patients with Gleason 8+ tumors are treated in an active manner. For patients with Gleason 6 tumors, a smaller fraction are treated in an active manner, but most are left with active surveillance. It is acknowledged that since the patient has impact in this decision process, the decision is of a subjective nature. A prognostic method in the field of deciding whether to treat a patient in an active manner would be most beneficial if decision support is provided for the borderline cases, i.e. for patients with Gleason 6-7 tumors.

Hence, the estimation of prognosis is a difficult task where improvements in current state-of-the-art would lead to great savings in the society. Of particular importance is to estimate if an individual diagnosed with PCa will require advanced therapy (surgery or radiation) or if the disease will be monitored by active surveillance. Advanced therapy has a number of serious side-effects, including impotence (predominantly for surgery), incontinence and gastrointestinal issues (the two latter predominantly for radiation therapy). This invention provides, however, predictive models for the prognosis of PCa through analysis of biomarkers and genetic profile of the individual diagnosed with PCa.

SUMMARY OF THE INVENTION

The present invention is based on the discovery that the combination of prognostic markers of different origin may improve the ability to determine if an individual diagnosed with PCa will require active or advanced therapy. This can result in major savings for the society, because aggressive cancers that are identified early are more easily treatable.

In the above-referenced patent application WO2012/031207A2, it is not disclosed how the method is applied in cases where SNP data is available for only a subset of the 33 SNP, in particular when data from more than 5% or more than 10% or more than 20% of the SNP are missing. This means that the method in WO2012/031207A2 may require that the tested individual is requested to supply a second sample for retesting of the genetic information that failed in the first test, should the first test lead to a partial result. It is further not disclosed how the method can be used for predicting therapy choice after diagnosis.

One aspect of the present invention provides a method based on a redundantly designed combination of data for estimating if an individual diagnosed with prostate cancer will require active therapy, comprising the steps of:

1. Providing at least one biological sample from said individual;
2. In said biological sample, analyzing a category of SNPs related to PCa (SNPpc), by measuring a presence or absence of each of a plurality of SNPpc;
3. Combining data regarding said category of SNPpc to form a SNPpc composite value, wherein the method allows disregarding a subset of at least 5% of the SNPpc of the SNPpc category when forming the SNPpc composite value;
4. Correlating said SNPpc composite value to the likelihood of the individual requiring active therapy, by comparing the SNPpc composite value to a pre-determined cut-off value established with control samples, wherein it is known if the individuals, from whom the control samples originate, required active therapy or did not require active therapy.

According to an aspect of the invention, one or more of the method steps, typically steps 3 and 4 are provided by means of a computer program product when executed in a computer comprising a processor and memory.

In an embodiment, step 3 of the above-described method is conducted with a computer programmed to form or calculate a SNPpc composite value from the data of step 2, and/or step 4 is conducted with a computer programmed to correlate the SNPpc composite value to the likelihood of the individual requiring active therapy by comparing the SNPpc composite value to a pre-determined cut-off value established with control samples, wherein it is known if the individuals, from whom the control samples originate, required active therapy or did not require active therapy. Additionally, the present invention relates to a non-transitory, tangible computer readable storage medium having executable instructions to conduct such calculations or form such composite values and/or to conduct the correlation step as described above.

The choice of cut-off value (or cut-off level) depends on many factors, including but not limited to the risk of the disease as such and the risk associated with inaccurately diagnosing an individual as positive who do not have the disease (false positive). The choice of cut-off value is described more in detail further below.

In an embodiment of the present invention, the SNP related to PCa (SNPpc) include at least two of rs11672691, rs11704416, rs3863641, rs12130132, rs4245739, rs3771570, rs7611694, rs1894292, rs6869841, rs2018334, rs16896742, rs2273669, rs1933488, rs11135910, rs3850699, rs11568818, rs1270884, rs8008270, rs4643253, rs684232, rs11650494, rs7241993, rs6062509, rs1041449, rs2405942, rs12621278, rs9364554, rs10486567, rs6465657, rs2928679, rs6983561, rs16901979, rs16902094, rs12418451, rs4430796, rs11649743, rs2735839, rs9623117, and rs138213197.

In an embodiment, the method further comprises analyzing, in said biological sample, a category of PCa biomarkers, by measuring a presence or concentration of each of a plurality of PCa biomarkers of said category of PCa biomarkers; combining data regarding said category of PCa biomarkers to form a biomarker composite value; combining the biomarker composite value and the SNPpc composite value to form an overall composite value; and correlating said overall composite value to the likelihood of said individual requiring active therapy by comparing the overall composite value to a pre-determined value established with control samples, wherein it is known if the individuals, from which the control samples originate, required active therapy or did not require active therapy.

Preferably, the method comprises measuring the presence or concentration of at least partially redundant PCa biomarkers, and wherein at least one, such as two, of the PCa biomarkers is selected from the group consisting of (i) PSA, (ii) total PSA (tPSA), (iii) intact PSA (iPSA), (iv) free PSA (fPSA), and (v) hK2.

More particularly, the method allows disregarding a subset of at least one of said PCa biomarkers (i)-(v) of the PCa biomarker category when forming said biomarker composite value, such as a subset of one, two, three, or four of said PCa biomarkers (i)-(v).

Further, in an embodiment, the method allows disregarding at least 10%, such as 15%, such as 20%, such as 30% of the SNPpc of the SNPpc category when forming the SNPpc composite value.

Preferably, the data regarding the category of PCa biomarkers are combined according to a predetermined equation to form said biomarker composite value, and/or the data regarding the category of SNPpc are combined according to a predetermined equation to form said SNPpc composite value. Also, said biomarker composite value and said SNPpc composite value are preferably combined according to a predetermined equation to form said overall composite value.

In an embodiment, the above method further comprises a step of recommending the individual for active therapy if the overall composite value is greater than the cut-off value.

In an embodiment, the method further comprises analyzing, in said biological sample, a category of SNPs related to a PCa biomarker concentration (SNPbm), by measuring a presence or absence of at least one SNPbm; combining data regarding said SNPbm to form a SNPbm composite value; and including the SNPbm composite value in the overall composite value.

In an embodiment, the SNPbm includes at least one of rs3213764, rs1354774, rs1227732, rs2736098, rs401681, rs10788160, rs11067228, rs1363120, rs888663, and rs1054564.

In an embodiment of the invention, the method further comprises analyzing, in said biological sample, a category of SNP related to the Body Mass Index of said individual (SNPbmi), by measuring a presence or absence of at least one SNPbmi; combining data regarding said category of SNPbmi to form a SNPbmi composite value; and including said SNPbmi composite value in the overall composite value.

In an embodiment, the SNPbmi includes at least one of rs3817334, rs10767664, rs2241423, rs7359397, rs7190603, rs571312, rs29941, rs2287019, rs2815752, rs713586, rs2867125, rs9816226, rs10938397, and rs1558902.

In another embodiment of the invention, the method further comprises collecting the family history regarding PCa, treatment history, and physical data from said individual; and wherein said family history, treatment history and/or physical data are included in the overall composite value.

In yet another embodiment, the method further comprises analyzing an additional category of PCa biomarkers, by measuring the presence or concentration of one or each of a plurality of PCa biomarkers of said additional biomarker category; combining data regarding said additional PCa biomarker category to form an additional biomarker composite value for said additional PCa biomarker category; and including said additional biomarker composite value in the overall composite value; wherein the combination of data to form the additional biomarker composite value is redundantly designed where the additional category of PCa biomarkers comprises more than one PCa biomarker.

In a preferred embodiment, the additional category of PCa biomarkers comprises the biomarker MIC-1 and optionally other MIC-1 related biomarkers, or the biomarker MSMB and optionally other MSMB related biomarkers.

In another embodiment, the method comprises analyzing each of a plurality of additional categories of PCa biomarkers and forming an additional biomarker composite value for each of the PCa biomarker categories, according to the above-described procedure. Preferably, at least two additional categories of PCa biomarkers are analyzed, wherein one additional category of PCa biomarkers comprises the biomarker MIC-1 and optionally other MIC-1 related biomarkers, and another additional category comprises the biomarker MSMB and optionally other MSMB related biomarkers.

In an embodiment, the biological sample is a blood sample.

In an embodiment of the invention, the overall composite value is calculated using a method in which the non-additive effect of a SNPbm and the corresponding PCa biomarker concentration is utilized.

In an embodiment of the method, the measurement of a presence or absence of the SNPs is conducted by use of MALDI mass spectrometry.

In an embodiment of the method, the measurement of a presence or concentration of the PCa biomarkers is conducted by use of microarray technology.

In a preferred embodiment of the method, the measurement of a presence or absence of a SNP (belonging to any category of SNPs) comprises measuring the number of alleles of said SNP. In an embodiment, one or two alleles corresponds to a presence of said SNP and zero alleles corresponds to an absence of said SNP in said individual; wherein zero alleles corresponds to homozygous negative for said SNP, one allele corresponds to heterozygous positive, and two alleles corresponds to homozygous positive.

In an embodiment, the above-described method comprises using an ELISA assay device, a microarray assay device, an immunoprecipitation assay device, an immuno-fluorescence assay device, a radio-immuno-assay device, or a mass spectrometry device using matrix-assisted laser desorption/ionization (MALDI), for the measurement of a presence or concentration of a PCa biomarker.

In an embodiment, which may be combined with the above-mentioned embodiment, the above-described method may comprise using a mass spectrometry device using matrix-assisted laser desorption/ionization (MALDI), for the measurement of a presence or absence of a SNP.

Another aspect of the present invention provides an assay device for performing step 2 (i.e. measuring a presence or absence of each of a plurality of SNPpc) of the above-described method for estimating if an individual diagnosed with prostate cancer will require active therapy, comprising a solid phase having immobilised thereon a category of ligands, which binds specifically to a SNPpc, and including a plurality of different ligands binding specifically to each of a plurality of SNPpc, such as at least one of rs11672691, rs11704416, rs3863641, rs12130132, rs4245739, rs3771570, rs7611694, rs1894292, rs6869841, rs2018334, rs16896742, rs2273669, rs1933488, rs11135910, rs3850699, rs11568818, rs1270884, rs8008270, rs4643253, rs684232, rs11650494, rs7241993, rs6062509, rs1041449, or rs2405942, rs12621278, rs9364554, rs10486567, rs6465657, rs2928679, rs6983561, rs16901979, rs16902094, rs12418451, rs4430796, rs11649743, rs2735839, rs9623117 and rs138213197.

In an embodiment, the assay device is further adapted for measuring a presence or concentration of at least one PCa biomarker, wherein the solid phase further has a second category of ligand immobilized which binds specifically to a PCa biomarker, and includes a plurality of different ligands binding specifically to each of a plurality of PCa biomarkers, such as at least one of PSA, iPSA, tPSA, fPSA, and hK2, and optionally MSMB and/or MIC-1.

In an embodiment, the assay device is further adapted for measuring a presence or absence of a SNPbm, in which case the solid phase further has a third category of ligand immobilized which binds specifically to a SNPbm, such as at least one of rs1227732, rs3213764, rs1354774, rs2736098, rs401681, rs10788160, rs11067228, rs1363120, rs888663, and rs1054564.

In an embodiment, the assay device is also adapted for measuring a presence or absence of a SNPbmi, in which case the solid phase further has a fourth category of ligand immobilized which binds specifically to a SNPbmi, such as at least one of rs3817334, rs10767664, rs2241423, rs7359397, rs7190603, rs571312, rs29941, rs2287019, rs2815752, rs713586, rs2867125, rs9816226, rs10938397, and rs1558902.

In an embodiment, the above-described assay device comprises an ELISA assay device, a microarray assay device, an immunoprecipitation assay device, an immuno-fluorescence assay device, a radio-immuno-assay device, or a mass spectrometry device using matrix-assisted laser desorption/ionization (MALDI), for the measurement of a presence or concentration of a PCa biomarker.

In an embodiment, which may be combined with the above-mentioned embodiment, the above-described assay device comprises a mass spectrometry device using matrix-assisted laser desorption/ionization (MALDI), for the measurement of a presence or absence of a SNP.

According to a further aspect of the invention, a test kit for performing step 2 (i.e. measuring a presence of each of a plurality of SNPpc) of the above-described method for estimating if an individual diagnosed with prostate cancer will require active therapy, comprising a corresponding assay device as described above, and a category of detection molecules, which is capable of detecting a SNPpc, such as at least one of rs11672691, rs11704416, rs3863641, rs12130132, rs4245739, rs3771570, rs7611694, rs1894292, rs6869841, rs2018334, rs16896742, rs2273669, rs1933488, rs11135910, rs3850699, rs11568818, rs1270884, rs8008270, rs4643253, rs684232, rs11650494, rs7241993, rs6062509, rs1041449, or rs2405942, rs12621278, rs9364554, rs10486567, rs6465657, rs2928679, rs6983561, rs16901979, rs16902094, rs12418451, rs4430796, rs11649743, rs2735839, rs9623117 and rs138213197.

In an embodiment, the test kit comprises an assay device that is further adapted for measuring a presence or concentration of at least one PCa biomarker, and a second category of detection molecule, which is capable of detecting a PCa biomarker, such as at least one of PSA, iPSA, tPSA, fPSA, and hK2, and optionally MSMB and/or MIC-1.

In an embodiment, the test kit comprises an assay device that is further adapted for measuring a presence or absence of at least one SNPbm, and a third category of detection molecule, which is capable of detecting a SNPbm, such as at least one of rs1227732, rs3213764, rs1354774, rs2736098, rs401681, rs10788160, rs11067228, rs1363120, rs888663, and rs1054564.

In an embodiment, the test kit comprises an assay device that is also adapted for measuring a presence or absence of a SNPbmi, and a fourth category of detection molecule, which is capable of detecting a SNPbmi, such as at least one of rs3817334, rs10767664, rs2241423, rs7359397, rs7190603, rs571312, rs29941, rs2287019, rs2815752, rs713586, rs2867125, rs9816226, rs10938397, and rs1558902.

Yet another aspect of the present invention provides an assay device comprising a solid phase having immobilized thereon a category of ligands, which binds specifically to a SNPpc, and including a plurality of different ligands binding specifically to each of a plurality of different SNPpc, selected from at least one of rs11672691, rs11704416, rs3863641, rs12130132, rs4245739, rs3771570, rs7611694, rs1894292, rs6869841, rs2018334, rs16896742, rs2273669, rs1933488, rs11135910, rs3850699, rs11568818, rs1270884, rs8008270, rs4643253, rs684232, rs11650494, rs7241993, rs6062509, rs1041449, or rs2405942, rs12621278, rs9364554, rs10486567, rs6465657, rs2928679, rs6983561, rs16901979, rs16902094, rs12418451, rs4430796, rs11649743, rs2735839, rs9623117 and rs138213197.

In an embodiment of the assay device, the solid phase further has a second category of ligand immobilized, which binds specifically to a PCa biomarker, and including a plurality of different ligands binding specifically to each of a plurality of different PCa biomarkers selected from at least one of PSA, iPSA, tPSA, fPSA, and hK2, and optionally MSMB and/or MIC-1.

In a further embodiment of the assay device, the solid phase further has a third category of ligand immobilized, which binds specifically to a SNPbm, and including one or a plurality of different ligands binding specifically to one or each of a plurality of SNPbm selected from at least one of rs1227732, rs3213764, rs1354774, rs2736098, rs401681, rs10788160, rs11067228, rs1363120, rs888663, and rs1054564.

In a further embodiment of the assay device, the solid phase further has a fourth category of ligand immobilized, which binds specifically to a SNPbmi, and including one or a plurality of different ligands binding specifically to one or each of a plurality of different SNPbmi selected from at least one of rs3817334, rs10767664, rs2241423, rs7359397, rs7190603, rs571312, rs29941, rs2287019, rs2815752, rs713586, rs2867125, rs9816226, rs10938397, and rs1558902.

Yet another aspect of the invention provides a computer program product directly loadable into the internal memory of a digital computer, characterized in that said product comprises software code means for performing at least step 3 (i.e. combining data regarding said category of SNPpc to form a SNPpc composite value) and step 4 (i.e. correlating said SNPpc composite value to the likelihood of the individual requiring active therapy, by comparing the SNPpc composite value to a pre-determined cut-off value established with control samples, wherein it is known if the individuals, from whom the control samples originate, required active therapy or did not require active therapy) of the above-described method for estimating if an individual diagnosed with prostate cancer will require active therapy; such as step 1 (i.e. providing at least one biological sample from said individual), step 2 (i.e. in said biological sample, analyzing a category of SNPpc by measuring a presence or absence of each of a plurality of SNPpc), step 3 and step 4 of said method.

In an embodiment, the computer program product further comprises software code means for determining a presence or concentration of at least one PCa biomarker.

In an embodiment, the computer program product further comprises software code means for analyzing a category of SNPbm by measuring a presence or absence of at least one SNPbm.

In an embodiment, the computer program product further comprises software code means for analyzing a category of SNPbmi by measuring a presence or absence of at least one SNPbmi.

A further aspect of the invention provides an apparatus comprising an assay device as described above and a corresponding computer program product as described above.

DETAILED DESCRIPTION OF THE INVENTION

Figure 1:
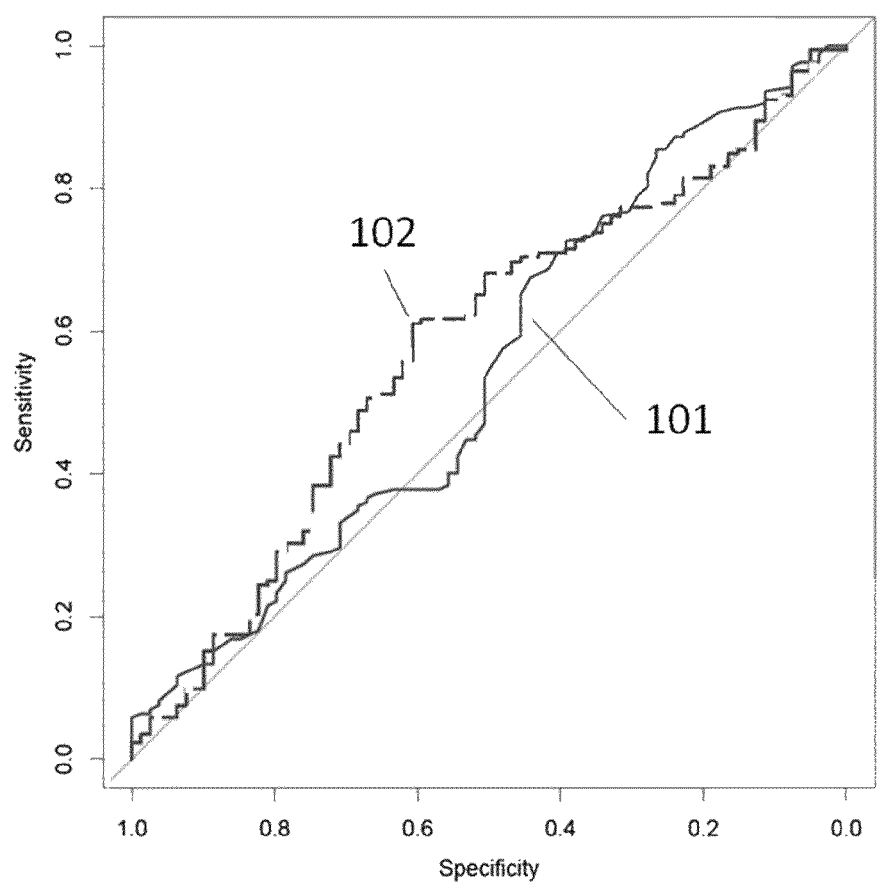
FIG. 1 shows the ROC curves for the linear model of Example 1 illustrating the difference in performance between PSA (101) and a genetic score model (102) in prediction if active treatment is required.

For the purpose of this application and for clarity, the following definitions are made:

The term "PSA" refers to serum prostate specific antigen in general. PSA exists in different forms, where the term "free PSA" refers to PSA that is unbound or not bound to another molecule, the term "bound PSA" refers to PSA that is bound or complexed to another molecule, and finally the term "total PSA" refers to the sum of free PSA and bound (complexed) PSA. The term "FIT PSA" is the ratio of unbound PSA to total PSA.

There are also molecular derivatives of PSA, where the term "proPSA" refers to a precursor inactive form of PSA and "intact PSA" refers to an additional form of proPSA that is found intact and inactive.

The term "diagnostic assay" refers to the detection of the presence or nature of a pathologic condition. It may be used interchangeably with "diagnostic method". Diagnostic assays differ in their sensitivity and specificity.

The term "prognostic assay" refers to the forecast of the development of an existing pathologic condition. It may be used interchangeably with "prognostic method".

Prognostic assays are, when providing a prognosis on if a particular event will occur, similar to diagnostic assays and may in such cases differ in their sensitivity and specificity. One such example is the prognostic assay forecasting if active therapy is required.

The term "active treatment" denotes treating a patient with PCa by surgery, by external radiation, by targeted radiotherapy, by chemotherapy, hypothermal therapy, hyperthermal therapy, or by any other medical procedure implemented for the purpose of treating PCa.

One measure of the usefulness of a diagnostic tool is "area under the receiver—operator characteristic curve", which is commonly known as ROC-AUC statistics. This widely accepted measure takes into account both the sensitivity and specificity of the tool. The ROC-AUC measure typically ranges from 0.5 to 1.0, where a value of 0.5 indicates the tool has no diagnostic value and a value of 1.0 indicates the tool has 100% sensitivity and 100% specificity.

The term "sensitivity" refers to the proportion of all subjects requiring active treatment that are correctly identified as such (which is equal to the number of true positives divided by the sum of the number of true positives and false negatives).

The term "specificity" refers to the proportion of all subjects not requiring active treatment (i.e. suitable for watchful waiting) that are correctly identified as such (which is equal to the number of true negatives divided by the sum of the number of true negatives and false positives).

The term "biomarker" refers to a protein, a part of a protein, a peptide or a polypeptide, which may be used as a biological marker, e.g. for diagnostic purposes.

The term "kallikrein-like biomarker" refers to protein biomarkers belonging to or being related to the kallikrein family of proteins, including but not limited to Prostate-specific antigen (PSA) in either free form or complexed form, pro PSA (a collection of isoforms of PSA) and in particular the truncated form (−2) pro PSA, intact PSA, human prostatic acid phosphatase (PAP), and human kallikrein 2 (abbreviated hK2 or HK2 or hk2 in the present application).

The term "single nucleotide polymorphism" (SNP) refer to the genetic properties of a defined locus in the genetic code of an individual. A SNP can be related to increased risk for PCa, and can hence be used for diagnostic or prognostic assessments of an individual. The Single Nucleotide Polymorphism Database (dbSNP) is an archive for genetic variation within and across different species developed and hosted by the National Center for Biotechnology Information (NCBI) in collaboration with the National Human Genome Research Institute (NHGRI), both located in the US. Although the name of the database implies a collection of one class of polymorphisms only (i.e., single nucleotide polymorphisms (SNP)), it in fact contains a range of molecular variation. Every unique submitted SNP record receives a reference SNP ID number ("rs#"; "refSNP cluster"). In this application, SNP are mainly identified using rs# numbers. Accordingly, within the present application, SNP is used to refer to the range of molecular variation as included in the dbSNP, rather than only single nucleotide polymorphisms. For the purpose of the present application, the terms "SNP" and "SNPs" may be used interchangeably, and may be used to describe the singular and/or the plural of "single nucleotide polymorphism".

The term "body-mass index" (BMI) refers to a heuristic proxy for human body fat based on an individual's weight and height, according to the formula BMI=weight/(height*height), where weight is the weight of an individual expressed in kilograms and height is the height of an individual expressed in meters. A normal healthy BMI value is typically considered to be within the range of 18.5 to 25, and individuals having BMI>30 are typically considered obese.

The term "medical history" refers to information related to historic examinations, diagnoses and/or therapy for any cancer disease. One non-limiting example of medical history is if a subject has been examined for the presence of PCa previously through biopsy of the prostate.

The term "parameter category" refers to a group or a family of related parameters, such as related biomarkers or related SNPs, which are partly or completely redundant in terms of predictive performance One example of a parameter category is "Kallikrein-like biomarkers", a category which includes for example PSA, total PSA (tPSA), intact PSA (iPSA), free PSA (fPSA), and hk2. Another example of a parameter category is "SNP related to BMI", a category which includes SNPs that are related to the BMI of an individual. In the prediction models of the present invention, it may be sufficient to have measurement results (data) for a subset of the members of each category, so as to make each category represented in the prediction model, albeit using only a subset of the members of the respective categories. The term "parameter category" is sometimes referred to as only "category" in the present application.

The term "composite value" refers to the combination of data related to a parameter category into a representative value for said parameter category. The combination of data can typically be performed according to one or more predetermined equations. A composite value is the output of the combination of data according to one or more predetermined equations. The different equations are applicable for different measurement results (i.e. data), depending on for which subsets of the members of the parameter category that data are available. One non-limiting example of a method to form a composite value for a particular parameter category is to use the average of the available results for the members of said category. The term "composite value" is sometimes referred to as "score" in the present application. One non-limiting example of a composite value is "biomarker composite value". Another non-limiting example of a composite value is "genetics composite value" (or "genetic score"), and more specifically "SNP composite value".

The term "redundantly designed combination of data" refers to a combination of data obtained by a plurality of measurements, to form a composite value for one or more parameter categories or subsets thereof, wherein the combination of data is performed such that a composite value representing one parameter category can be produced based either on a subset of data, e.g. where some data are missing or erroneous, or on the full set of data.

The term "a plurality" as used in the present application means "two or more".

The present invention provides prognostic methods to aid in indicating, estimating, detecting and/or determining whether an individual shall be recommended active therapy for PCa. The present invention can, if desired, be tailored to defined subpopulations in order to increase the performance and the usefulness of the invention within said subpopulation. Even though the present invention can be applied to the general population of male individuals, it is possible to construct methods for indicating, estimating, detecting or determining whether an individual shall be recommended active therapy for PCa with enhanced performance for defined subpopulations, including but not limited to, individuals having PSA value lower than approximately 7 ng/mL (i.e. lower than a predetermined value between 1 ng/mL and 30 ng/mL) or a concentration of free PSA lower than approximately 0.91 ng/mL (i.e. lower than a predetermined value between 0.1 ng/mL and 3 ng/mL).

The basic principle of the invention is the use of combinations of biomarkers and genetic information in such a manner that the combinatorial use of the assessed information about the individual improves the quality of the prognosis.

Collecting the family history regarding PCa from said patient (Category HIST).

Collecting patient physical data, such as weight, BMI, age and similar (Category PPD)

Obtaining a number of biological samples from said patient.

In said biological samples, measuring or quantifying the presence or concentration of a plurality of defined biomarkers (Category Biomarker), followed by combining data regarding said biomarkers to form a biomarker composite value.

In said biological samples, measuring or quantifying the genetic status of said patients with respect to a plurality of defined SNPs related to PCa (Category SNPpc), by measuring or quantifying the presence or absence of a plurality of defined SNPs related to PCa (SNPpc), and followed by combining data obtained regarding the SNPs related to PCa, to form a SNPpc composite value.

In said biological samples, measuring or quantifying the genetic status of said patients with respect to a plurality of defined SNPs related to biomarker expression level or biomarker concentration (Category SNPbm), by measuring or quantifying the presence or absence of a plurality of defined SNPs related to biomarker expression level or biomarker concentration (SNPbm), to form a SNPbm composite value.

The composite value for at least one of the categories as defined above is used for estimating the prognosis of prostate cancer. Commonly, the composite values for at least two of the categories as defined above are combined to form an overall composite value for the use in estimating the prognosis of prostate cancer.

Determining by using said category composite value or overall composite value, alone or in combination with further data, if the patient is likely to require advanced treatment for PCa.

In more detail, the step comprising the collection of family history includes, but is not limited to, the identification of if any closely related male family member (such as the father, brother or son of the patient) suffers or have suffered from PCa.

Physical information regarding the patient is typically obtained through a regular physical examination wherein age, weight, height, BMI and similar physical data are collected.

Collecting biological samples from a patient includes, but is not limited to plasma, serum, DNA from peripheral white blood cells and urine.

The quantification of presence or concentration of biomarkers in a biological sample can be made in many different ways. One common method is the use of enzyme linked immunosorbent assays (ELISA) which uses antibodies and a calibration curve to assess the presence and (where possible) the concentration of a selected biomarker. ELISA assays are common and known in the art, as evident from the publication "Association between saliva PSA and serum PSA in conditions with prostate adenocarcinoma." by Shiiki N and co-authors, published in Biomarkers. 2011 September; 16(6):498-503, which is incorporated by reference herein. Another common method is the use of a microarray assay for the quantification of presence or concentration of biomarkers in a biological sample. A typical microarray assay comprises a flat glass slide onto which a plurality of different capture reagents (typically an antibody) each selected to specifically capture one type of biomarker is attached in non-overlapping areas on one side of the slide. The biological sample is allowed to contact, for a defined period of time, the area where said capture reagents are located, followed by washing the area of capture reagents. At this point, in case the sought-after biomarker was present in the biological sample, the corresponding capture reagent will have captured a fraction of the sought-after biomarker and keep it attached to the glass slide also after the wash.

Next, a set of detection reagents are added to the area of capture reagents (which now potentially holds biomarkers bound), said detection reagents being capable of (i) binding to the biomarker as presented on the glass slide and (ii) producing a detectable signal (normally through conjugation to a fluorescent dye). It is typically required that one detection reagent per biomarker is added to the glass slide. There are many other methods capable of quantifying the presence or concentration of a biomarker, including, but not limited to, immunoprecipitation assays, immunofluorescense assays, radio-immuno-assays, and mass spectrometry using matrix-assisted laser desorption/ionization (MALDI), to mention a few examples.

The quantification of presence of SNPs through the analysis of a biological sample typically involves MALDI mass spectrometry analysis based on allele-specific primer extensions, even though other methods are equally applicable. This applies to any type of SNP, i.e. both SNPs related to PCa (SNPpc), SNPs related to the BMI (SNPbmi), and SNPs related to biomarker expression/concentration (SNPbm).

The combination of data can be any kind of algorithmic combination of results, such as a linear combination of data wherein the linear combination improves the diagnostic performance (for example as measured using ROC-AUC). Other possible methods for combining into a model capable of producing a diagnostic estimate include (but are not limited to) non-linear polynomials, support vector machines, neural network classifiers, discriminant analysis, random forest, gradient boosting, partial least squares, ridge regression, lasso, elastic nets, k-nearest neighbors. Furthermore, the book "The Elements of Statistical Learning: Data Mining, Inference, and Prediction, Second Edition" by T Hastie, R Tibshirani and J Friedman as published by Springer Series in Statistics, ISBN 978-0387848570 (which is incorporated by reference herein) describes many suitable methods for combining data in order to predict or classify a particular outcome.

Suitable biomarkers for making prognoses of PCa include, but are not limited to, Prostate-specific antigen (PSA) in either free form or complexed form, pro PSA (a collection of isoforms of PSA) and in particular the truncated form (−2) pro PSA, intact PSA, human prostatic acid phosphatase (PAP), human kallikrein π (hK2), early prostate cancer antigen (EPCA), Prostate Secretory Protein (PSP94; also known as beta-microseminoprotein and MSMB), glutathione S-transferase it (GSTP1), and α-methylacyl coenzyme A racemase (AMACR). Related biomarkers, which may be useful for improving the diagnostic accuracy of the method includes Macrophage Inhibitory Cytokine 1 (MIC-1; also known as GDF-15).

Suitable SNPs related to PCa include, but are not limited to rs12621278 (Chromosome 2, locus 2q31.1), rs9364554 (Chromosome 6, locus 6q25.3), rs10486567 (Chromosome 7, locus 7p15.2), rs6465657 (Chromosome 7, locus 7q21.3), rs2928679 (Chromosome 8, locus 8p21), rs6983561 (Chromosome 8, locus 8q24.21), rs16901979 (Chromosome 8, locus 8q24.21), rs16902094 (Chromosome 8, locus 8q24.21), rs12418451 (Chromosome 11, locus 11q13.2), rs4430796 (Chromosome 17, locus 17q12), rs11649743 (Chromosome 17, locus 17q12), rs2735839 (Chromosome 19, locus 19q13.33), rs9623117 (Chromosome 22, locus 22q13.1), and rs138213197 (Chromosome 17, locus 17q21)

Suitable SNPs related to PCa further include, but are not limited to rs11672691, rs11704416, rs3863641, rs12130132, rs4245739, rs3771570, rs7611694, rs1894292, rs6869841, rs2018334, rs16896742, rs2273669, rs1933488, rs11135910, rs3850699, rs11568818, rs1270884, rs8008270, rs4643253, rs684232, rs11650494, rs7241993, rs6062509, rs1041449, and rs2405942.

Suitable SNPs related to PCa further include, but are not limited to rs138213197 as described in the report "Germline mutations in HOXB13 and prostate-cancer risk." by Ewing CM and co-authors as published in N Engl J Med. 2012 Jan. 12; 366(2):141-9 (which is incorporated by reference herein), 1100delC (22q12.1) and I157T (22q12.1) as described in the report "A novel founder CHEK2 mutation is associated with increased prostate cancer risk." by Cybulski C and co-authors as published in Cancer Res. 2004 Apr. 15; 64(8):2677-9 (which is incorporated by reference herein), and 657del5 (8q21) as described in the report "NBS1 is a prostate cancer susceptibility gene" by Cybulski C and co-authors as published in Cancer Res. 2004 Feb. 15; 64(4):1215-9 (which is incorporated by reference herein).

It is possible to define a parameter category as "SNP related to PCa" which includes SNP related to PCa. Suitable members include (but are not limited to) the SNPs listed above. A subset of the members of this category would be sufficient to represent the category as such in a predictive model.

Suitable SNPs related to other processes than PCa further include, but are not limited to rs3213764, rs1354774, rs2736098, rs401681, rs10788160 rs11067228, all being related to the expression level of PSA. It is possible to define a parameter category as "SNP related to concentration of PSA" or "SNP related to expression level of PSA" which includes SNP related to the concentration or expression level of PSA. A subset of the members of this category would be sufficient to represent the category as such in a predictive model. The SNP rs3213764 and rs1354774 relate particularly to the expression level of free PSA.

Suitable SNPs related to other processes than PCa include, but are not limited to rs1363120, rs888663, rs1227732, rs1054564, all being related to the expression level of the inflammation cytokine biomarker MIC1. It is possible to define a parameter category as "SNP related to concentration of MIC1" or "SNP related to expression level of MIC1" which includes SNP related to the concentration or expression level of MIC1. A subset of the members of this category would be sufficient to represent the category as such in a predictive model.

It is possible to define a parameter category as "SNP related to PCa biomarker concentration" or "SNP related to PCa biomarker expression level" which includes SNP related to the concentration or expression level of relevant biomarkers such as Prostate-specific antigen (PSA) in either free form or complexed form, pro PSA (a collection of isoforms of PSA) and in particular the truncated form (−2) pro PSA, intact PSA, human prostatic acid phosphatase (PAP), human kallikrein 2 (hK2), early prostate cancer antigen (EPCA), Prostate Secretory Protein (PSP94; also known as beta-microseminoprotein and MSMB), glutathione S-transferase π (GSTP1), α-methylacyl coenzyme A racemase (AMACR), and Macrophage Inhibitory Cytokine 1 (MIC-1; also known as GDF-15). A subset of the members of this category would be sufficient to represent the category as such in a predictive model.

Suitable SNPs related to other processes than PCa further include, but are not limited to rs3817334, rs10767664, rs2241423, rs7359397, rs7190603, rs571312, rs29941, rs2287019, rs2815752, rs713586, rs2867125, rs9816226, rs10938397, and rs1558902 all being related to the BMI of an individual. Other suitable SNP related to BMI are disclosed in the report "Contribution of 32 GWAS-identified common variants to severe obesity in European adults referred for bariatric surgery" by Magi and co-authors as published in PLoS One. 2013 Aug. 7; 8(8):e70735 (which is incorporated by reference herein). It is possible to define a parameter category as "SNP related to expression level of BMI" which includes SNP related to the BMI of the individual. A subset of the members of this category would be sufficient to represent the category as such in a predictive model.

A preferred collection of SNP to be used in the assessment of the presence or non-presence of aggressive prostate cancer in a subject is rs582598, rs439378, rs2207790, rs1046011, rs10458360, rs7525167, rs10489871, rs7529518, rs4245739, rs4512641, rs10178804, rs11900952, rs1873555, rs10191478, rs6755901, rs6545962, rs721048, rs2710647, rs12612891, rs2028900, rs1009, rs12233245, rs6760417, rs10496470, rs10199796, rs12475433, rs16860513, rs12151618, rs3765065, rs13017302, rs12988652, rs871688, rs749264, rs3771570, rs4346531, rs6770955, rs12637074, rs2660753, rs13319878, rs6437715, rs2162185, rs1515542, rs2270785, rs9830294, rs1439024, rs6762443, rs888507, rs6794467, rs12490248, rs1477886, rs4833103, rs3796547, rs17779822, rs2366711, rs16849146, rs1894292, rs12640320, rs3805284, rs12500426, rs4699312, rs17021918, rs7679673, rs2047408, rs2647262, rs12506850, rs7658048, rs2078277, rs12505546, rs13113975, rs4246742, rs2736098, rs401681, rs11134144, rs10060513, rs40485, rs2087724, rs1482679, rs16901841, rs1295683, rs2070874, rs7752029, rs2018334, rs9358913, rs1140809, rs409558, rs3096702, rs9267911, rs2025645, rs9359428, rs6569371, rs2813532, rs1933488, rs712242, rs6934898, rs9456490, rs651164, rs3120137, rs9364554, rs9457937, rs10486562, rs10807843, rs7801918, rs6962297, rs2465796, rs6957416, rs7777631, rs2272316, rs6961773, rs2132276, rs13265330, rs16887736, rs2911756, rs2272668, rs2339654, rs1380862, rs9297746, rs12543663, rs10086908, rs16901922, rs1016343, rs17832285, rs16901979, rs4871779, rs10107982, rs16902094, rs620861, rs17467139, rs6983267, rs9297756, rs10094059, rs7818556, rs1992833, rs986472, rs12552397, rs4273907, rs4237185, rs753032, rs11253002, rs2386841, rs10795841, rs10508422, rs7075945, rs10508678, rs539357, rs10826398, rs3818714, rs7090755, rs10993994, rs4382847, rs1891158, rs10887926, rs10788160, rs6579002, rs10832514, rs7358335, rs1944047, rs3019779, rs10896437, rs12793759, rs7106762, rs7102758, rs2449600, rs585197, rs2509867, rs11568818, rs7125415, rs11601037, rs11222496, rs4570588, rs6489721, rs3213764, rs17395631, rs4423250, rs11168936, rs10875943, rs3759129, rs902774, rs1827611, rs4760442, rs11610799, rs6539333, rs11067228, rs7485441, rs6489794, rs4119478, rs17070292, rs2293710, rs17256058, rs1950198, rs2331780, rs7141529, rs12880777, rs17123359, rs785437, rs524908, rs12903579, rs7178085, rs7164364, rs896615, rs11634741, rs9972541, rs12594014, rs11631109, rs1558902, rs8044335, rs2738571, rs885479, rs385894, rs684232, rs4925094, rs17138478, rs11649743, rs2107131, rs7213769, rs12946864, rs306801, rs138213197, rs1863610, rs17224342, rs9911515, rs12947919, rs966304, rs17744022, rs7234917, rs1943821, rs2227270, rs1363120, rs888663, rs1227732, rs1054564, rs4806120, rs11672691, rs758643, rs3745233, rs6509345, rs2659051, rs2735839, rs1354774, rs2691274, rs6090461, rs2297434, rs6062509, rs2315654, rs2823118, rs2838053, rs398146, rs16988279, rs2269640, rs4822763, rs132774, rs747745, rs5978944, rs6530238, rs5934705, rs5935063, rs4830488, rs17318620, rs5945619, rs5945637, rs11091768, rs2473057, rs5918762, rs4844228, rs6625760 and rs17324573. Even though the use of the complete list is preferable, any subset of this list is suitable for use in the assessment of the presence or nonpresence of aggressive prostate cancer in a subject. The SNP in this list (all, or a subset comprising about 95%, or 90%, or 85%, or 80%, or 75%, or 70%, of the SNP in this list) may be placed on the same solid support, for example the same glass slide, for simultaneous detection in a suitable analytical instrument.

One inevitable consequence of the difficulties in obtaining accurate and comparable estimates of the predictive performance of any given diagnostic or prognostic model in the screening of PCa is that when calculating the relative improvement of a novel method as compared to using PSA alone, the calculated relative improvement will vary depending on many factors. One important factor that influences the calculated relative improvement is how the control group (i.e. known negatives) is obtained. For example, since it is unethical to conduct biopsies on subjects where there are no indications of PCa, the control group will often be selected with bias. Thus, the relative improvement of a novel method will depend on how the control group was selected. Any reported estimated improvement must therefore be seen in the light of such variance. To the best of our experience, for diagnostic assays we estimate that if the relative improvement of a novel method is reported to be 15% as compared to the PSA value alone using one fair method for selecting the control group, said method would be at least 10% better than the PSA value alone using any other fair method for selecting the control group. For prognostic assays the comparison with a golden standard is equally difficult and any statement on prognostic assay performance (in this document and elsewhere) must be seen in the light of the variance induced by the choice of control group.

One possible method for obtaining a screening method for PCa meeting the requirements for widespread use is to combine information from multiple sources. From an overview level, this comprises combining values obtained from biomarker analysis (e.g. PSA values), genetic profiles (e.g. the SNP profile), family history, and other sources. The combination as such has the possibility to produce a better diagnostic statement than any of the included factors alone. Attempts to combine values into a multiparametric model to produce better diagnostic statements have been disclosed, as described elsewhere in the current application. The same approach can be applied for prognostic methods.

The algorithm which turns the data from the different categories into a single value being indicative of if the patient is likely to suffer from PCa is preferably a non-linear function, wherein the dependency of different categories is employed for further increasing the diagnostic performance of the method. For example, one important dependency is the measured level of a selected biomarker combined with any associated genetic marker related to the expected expression level of said biomarker. In cases where an elevated concentration of the biomarker is found in a patient sample, and at the same time said patient is genetically predisposed of having lower levels of said biomarkers, the importance of the elevated biomarker level is increased. Likewise, if a biomarker level is clearly lower than normal in a patient being genetically predisposed to have high levels of said biomarkers, the contradictory finding increases the importance of the biomarker level interpretation.

The algorithm used for predicting preferred therapy may benefit from using transformed variables, for example by using the log 10(PSA) value. Transformation is particularly beneficial for variables with a distribution that is deviating clearly from the normal distribution. Possible variable transformations include, but are not limited to, logarithm, inverse, square, and square root. It is further common to center each variable to zero average and unit variance.

Although the combining of data can be performed in different ways, a typical procedure according to the present invention can be illustrated in the following non-limiting manner.

In a typical case, data regarding biomarkers belonging to a parameter category will be combined according to a predetermined equation to form a composite value which is related to the risk related to the parameter category as such. One non-limiting example is to calculate the average value of all available measurement values (data) for the members of a biomarker category, and use said average value as the composite value representing said biomarker category. This procedure may clearly be applied regardless of how many biomarker members belong to the category. If only data for one of the biomarkers included in a category is available, it can be used in itself to represent the biomarker category. For biomarkers, the measured value commonly used in the step of combination of data is the concentration of said biomarker found in the biological sample. For example, for the biomarkers PSA and HK2, this is most commonly the concentration of biomarker in a blood sample as expressed in units ng/mL.

The genetic score (i.e. the genetics composite value, or more specifically the SNP composite value) calculation is typically based on a predetermined odds ratio for each individual SNP included in a parameter category. For each SNP the odds ratio, i.e. the likelihood that an individual who carries a SNP (i.e. has the risk allele defined by the SNP) has the disease or condition under study, is determined in advance. Determination of the odds ratio for a SNP is usually done in large prospective studies involving thousands of subjects with known conditions or diseases.

The genetic score for an individual can, as a non-limiting example, be computed according to the following algorithm: For the individual at test, each SNP is processed in the following manner. For each SNP the individual may carry two SNP risk alleles (homozygous positive for said SNP), or one risk allele (heterozygous positive for said SNP) or zero risk alleles (homozygous negative for said SNP). The number of alleles for a SNP is multiplied with the natural logarithm of the odds ratio for said SNP to form a risk assessment value for that particular SNP. This means that an individual who is negative for a particular SNP (i.e. has zero SNP risk alleles) will have no risk contribution from said particular SNP. This procedure is repeated for all SNP for which measurement data is available. When all risk assessment values have been calculated, the average of the risk contribution for the SNP for which measurement data are available is calculated and is used as the genetic score for said individual, i.e. the genetics composite value with respect to a certain category of SNPs. This procedure may clearly be applied regardless of how many SNP members belong to the SNP category.

To further illustrate a typical procedure according to the present invention, when applied to an individual, the following assumptions are made. Two parameter categories are defined, firstly a protein biomarker category (or biomarker category) having the members Prot1 and Prot2, and secondly a genetic category (or more specifically, a SNP category) having the members Snp1, Snp2, and Snp3. In an experiment involving 100 individuals with the known condition C and 100 individuals known not to have condition C, the relationship of Prot1, Prot2, Snp1, Snp2, and Snp3 with the condition C is established and formulated as one protein biomarker composite value for Prot1 and Prot2, and one genetic composite value for Snp1, Snp2, and Snp3, and also one overall composite value which in turn is related to the risk of having condition C. The composite value for the protein biomarker category is calculated using the following predetermined equations:

P=(Prot1+2*Prot2)/3 [if data regarding both Prot1 and Prot2 (i.e. both Prot1 value and Prot2 value) are available]

P'=Prot1 [in case only data regarding Prot1 (i.e. the Prot1 value) is available]

P"=Prot2 [in case only data regarding Prot2 (i.e. the Prot2 value) is available]

Hence, in this hypothetical case it was found in the experiment that (a) Prot1 and Prot2 has the same scale and (b) the value of Prot2 is twice as important for assessing if an individual has condition C than Prot 1. If only data for one of the protein biomarkers is available it can be used in itself to represent the protein biomarker category.

The odds ratios for the members of the genetic category had been determined in advance and were the following: Snp1=1.1; Snp2=1.2; and Snp3=1.3. The composite value for the genetic category is calculated as the genetic score described above.

The protein biomarker composite value and the genetic score (which in this case is equivalent to the genetic category composite value, or the SNP composite value) are then combined into an overall composite value according to the following predetermined equation:

$$Y=P+10*score$$

where Y is related to the risk of having condition C, P is the protein biomarker composite value (and P may be substituted by P' or P" as defined above), and score is the genetic score. All equations need to be developed based on a large group of individuals, in this hypothetical case the 100+100 individuals, in which the relationship between Y and the disease or condition under study is derived. In this hypothetical case it is assumed that if Y>5 the risk for the individual to have condition C is elevated and if Y>10 the risk is very high.

Now assume that a first individual A is being tested for Prot1, Prot2, Snp1, Snp2, and Snp3. In this particular case, all measurements were successful and produced the following results:

Prot1=3 ng/mL
Prot2=6 ng/mL
Snp1=homozygous negative i.e. no risk alleles=0
Snp2=heterozygous positive, i.e. one risk allele=1
Snp3=homozygous positive, i.e. two risk alleles=2

The composite value for the protein biomarker category will in this case be P=(3+2*6)/3=5. The composite value for the genetic category, also known as the genetic score, becomes score=(0*log(1.1)+1*log(1.2)+2*log(1.3))/3=0.2357. The overall composite value becomes Y=5+10*0.2357=7.357. Hence, the risk of having condition C for the individual A is estimated to be elevated but not very high.

Now further assume that a second individual B is being tested for Prot1, Prot2, Snp1, Snp2, and Snp3. In this particular case, three measurements were successful and produced the following results:

Prot1=2 ng/mL
Prot2=MISSING DATA
Snp1=homozygous positive, i.e. two risk alleles=2
Snp2=MISSING DATA
Snp3=heterozygous positive, i.e. one risk allele=1

The composite value for the protein biomarker category will in this case be P'=2, because only Prot1 results are available. The composite value for the genetic category, also known as the genetic score, becomes score=(2*log(1.1)+1*log(1.3))/2=0.2264. The overall composite value becomes Y=2+10*0.2264=4.264. Hence, the risk for the individual B of having condition C is estimated to be low.

Generally, in models predicting the risk for developing aPCa, there is often one or more cut-off values defined. The choice of cut-off value (or cut-off level) depends on many factors, including but not limited to the risk of the disease as such and the risk associated with inaccurately diagnosing an individual as positive who do not have the disease (false positive). In the general case, a predictive model is usually a monotonic function Y=f(x1, x2, . . . , xN) where the estimated risk of having the disease is correlated with the increasing value of Y. This means that if the cut-off value is set at a low level, the test will produce a large number of false positive results, but will on the other hand detect most individuals that actually have the disease. If the cut-off level is set at a high value the opposite occurs where individuals having a Y value above the cut-off level will with very high probability have the disease, but a large number of individuals with disease will receive a negative test results (i.e. large number of false negative results). The choice of cut-off level depends on many factors, including the socio-economic outcome of balancing (a) missing individuals with the disease and (b) treating individuals without the disease.

When applied in practice, it will occasionally happen that one or a few measurements fail due to for example unforeseen technical problems, human error, or any other unexpected and uncommon reason. In such cases the data set obtained for an individual will be incomplete. Typically, such an incomplete data set would be difficult or even impossible to evaluate. However, the current invention relies on measurements of a large number of features of which many are partially redundant. This means that also for individuals for which the data set is incomplete, it will in many cases be possible to produce a high-quality assessment according to the invention. This is particularly true within categories, where for example the kallikrein-like biomarkers are correlated and partially redundant. Technically, it is therefore possible to apply an algorithmic two-step approach, wherein the kallikrein biomarker contribution is summarized into a kallikrein score (or kallikrein value). This kallikrein score is then in a second step being combined with other data (such as genetic score, age, and family history to mention a few non-limiting examples) to produce a diagnostic or prognostic statement on PCa. Similar two-step procedures can be implemented for other classes of markers, such as genetic markers related to BMI or protein biomarkers related to transforming growth factor beta superfamily (a large family of structurally related cell regulatory proteins that includes MIC-1), to mention two non-limiting examples.

The redundancy aspect can be embodied in many different manners. One possible way to implement the redundancy aspect is to define a set of biomarkers representing biomarkers related to a common field or family. One non-limiting example of such a field or family is kallikrein-like biomarkers. More than one defined set (or category) of biomarkers can be determined, and in addition still other biomarkers can be applied outside such a set.

Typically, the categories are non-overlapping, i.e. any defined biomarker is only member of one defined category or used in a solitary manner Next, for all biomarkers an attempt to determine a presence or concentration is made. In most cases the determination for all biomarkers will succeed, but occasionally one or a few values will be missing. To induce model robustness to missing values, it is possible to define a biomarker category composite value which can be determined using all or a subset of the members of the defined category. To work in practice, this requires that the members of the defined category of biomarkers are at least partially redundant. In the next step, the biomarker category composite value is combined with other biomarker values, other biomarker category composite values (if two or more categories of biomarkers were defined), genetic score related to PCa risk, genetic score related to other features (such as BMI or biomarker concentration, to mention two non-limiting examples), family history, age, and other information carriers related to the assessment of preferred therapy into an overall composite value. The overall composite value is finally used for the estimation of preferred therapy.

The purpose of the biomarker category composite value is hence to serve as an intermediate value which can be estimated using incomplete data. Assume that a defined category of biomarkers comprises N different biomarkers denoted B1, B2, B3, . . . BN, all related to the biomarker family B. In that case, there could be N different models available for calculating the family B biomarker composite value C:

$C = f1(B1, B2, B3, \ldots BN)$
$C = f2(B2, B3, \ldots BN)$
$C = f3(B1, B3, \ldots BN)$
. . .
$C = fN(B1, B2, B3, \ldots BN-1)$ Wherein $f1(\ ), f2(\ ) \ldots fN(\ )$ are mathematical functions using the values for biomarkers B1, . . . BN as input and in some manner producing a single output C representing family B biomarker composite value. One non-limiting example of the functions $f1(\ ) \ldots fN(\ )$ include linear combinations of the present arguments. With such a set of multiple functions capable of calculating C for all the cases of one single biomarker value missing, the calculation of the overall composite value becomes less sensitive to missing data. It is understood that the estimate of C might be of less good quality when not all data is present, but may still be good enough for use in the assessment of preferred therapy. Thus, using such a strategy, only N−1 biomarker determinations have to succeed in order to produce an estimate of C. It is further possible to develop estimates for any number of lost data, i.e. if N−2 biomarker determinations have to succeed, another set of functions $f(\ )$ could be developed and applied to estimate C.

Thus, with respect to PCa biomarkers, the present invention relates to a method that is based on a redundantly designed combination of data, as defined elsewhere in the present application. More specifically, the method comprises measuring the presence or concentration of at least partially redundant PCa biomarkers, and wherein at least one, such as two, of the PCa biomarkers is selected from the group consisting of (i) PSA, (ii) total PSA (tPSA), (iii) intact PSA (iPSA), (iv) free PSA (fPSA), and (v) hK2. The method allows disregarding a subset of at least one of the PCa biomarkers (i)-(v) when forming the biomarker composite value. In other words, the method allows that the biomarker composite value is formed from data regarding less than all PCa biomarkers of the biomarker category, more specifically data regarding a subset of at most four of said PCa biomarkers. As the skilled person will appreciate, this will be equivalent to a method where data regarding a subset of at most four of said PCa biomarkers are required to form said biomarker composite value. It is an advantage of the method according to the present invention that omission, lack, or loss of data regarding a subset of said PCa biomarkers is acceptable when forming the biomarker composite value.

As the skilled person will appreciate, the present invention includes that the method comprises forming the biomarker composite value from data regarding all biomarkers of the biomarker category, provided that data regarding all biomarkers are available.

In an embodiment, the method allows disregarding a subset of one, two, three, or four of the PCa biomarkers (i) PSA, (ii) total PSA (tPSA), (iii) intact PSA (iPSA), (iv) free PSA (fPSA), and (v) hK2. In other words, the method allows that said biomarker composite value is formed from data regarding a subset of four, three, two or one of the PCa biomarkers (i)-(v), respectively.

As mentioned earlier in the present application, the method may further comprise analyzing one or each of a plurality of additional categories of PCa biomarkers, wherein the combination of data to form each additional biomarker composite value is redundantly designed where the additional category of PCa biomarkers comprises more than one PCa biomarker. The method allows disregarding a subset of the PCa biomarkers when forming the biomarker composite value. In other words, the method allows that the biomarker composite value is formed from data regarding less than all PCa biomarkers of the additional biomarker category, such as data regarding a subset of 10%, 20%, 30%, 40%, 50%, 60%, 70%, 80%, or 90% of the PCa biomarkers of the additional PCa biomarker category. As the skilled person will appreciate, the present invention includes that the method comprises forming each additional biomarker composite value from data regarding all PCa biomarkers of the PCa biomarker category, provided that data regarding all PCa biomarkers are available.

Genetic risk scores (i.e. genetic scores, or genetics composite values, more particularly SNP composite values) are also insensitive to small losses of data due to for example unforeseen technical problems, human error, or any other unexpected and uncommon reason. The contribution of one snp to the risk score is typically not correlated to any other snp. In the case of snp, the risk change due to each snp is small, but by using multiple snp related to a condition in concert, the risk change for said condition becomes large enough for having an impact on the model performance. The preferred number of snp to form a genetic score is at least 3 snp, more preferably 10 snp, more preferably 25 snp, still more preferably 50 snp, more preferably, 60 snp, still more preferably 70 snp, yet more preferably 80 snp, more preferably 90 snp, yet more preferably 100 snp, still more preferably 150 snp, yet more preferably 200 snp, still more preferably 250, and still even more preferably 300 snp. This means that the impact of any single snp on the total result is typically small, and the omission of a few snp will typically not alter the overall genetic score risk assessment in any large manner, i.e. will typically not alter the SNP composite value to a significant extent. In current state of the art, the typical data loss in the large scale genetic measurements is on the order of 1-2%, meaning that if a genetic score is composed of 100 different snp, the typical genetic characterization of an individual would provide information about 98-99 of these snp's. The present model as such, as discovered in the work of the present invention, can however withstand a larger loss or lack of data, such as 5-7% loss of information, or 7-15%, or even 15-30%. In this sense, the combination of data regarding SNPpc is at least partially redundant.

Consequently, also with respect to genetic markers (SNPs), the present invention relates to a method that is based on a redundantly designed combination of data, as defined elsewhere in the present application. The method allows disregarding at least 5% of the SNPpc when forming the SNP composite value. In other words, the method allows that said SNPpc composite value is formed from data regarding less than all SNPpc of the SNPpc category, more specifically data regarding a subset of at most 95% of said SNPpc. As the skilled person will appreciate, this will be equivalent to a method where data regarding a subset of at most 95% of said SNPpc are required to form said SNPpc composite value. It is an advantage of the method according to the present invention that omission, lack, or loss of data regarding a subset of said SNPpc is acceptable when forming the SNPpc composite value.

As the skilled person will appreciate, the present invention includes that the method comprises forming the SNPpc composite value from data regarding all SNPpc of the SNPpc category, if data regarding all SNPpc are available. Similarly, the present invention includes that the method comprises forming the SNPpc composite value from data regarding a subset of 99%, 98%, 97%, or 96% of said SNPpc.

In an embodiment, the method allows disregarding 6%, 7%, 8%, 9%, 10%, 15%, 20%, 25%, or 30% of the SNPpc when forming the SNPpc composite value. In other words, the method allows that said SNPpc composite value is formed from data regarding a subset of 94%, 93%, 92%, 91%, 90%, 85%, 80%, 75%, or 70% of the SNPpc, respectively.

One non-limiting example of such a redundantly designed combination of data is a calculation of the average of the risk related to each SNP for which measurement data exist. Another non-limiting example of such a redundantly designed combination of data is to provide multiple independent equations to calculate the composite value, one equation for each subset of data that can be used to produce said composite value.

One suitable method for associating a SNP with a condition (for example PCa, or elevated hk2 biomarker concentration in blood) has been described in the public report "Blood Biomarker Levels to Aid Discovery of Cancer-Related Single-Nucleotide Polymorphisms: Kallikreins and Prostate Cancer" by Robert Klein and co-authors as published in Cancer Prev Res 2010; 3:611-619 (which is incorporated by reference herein). In this report, the authors describe how they could associate the SNP rs2735839 to elevated value of (free PSA)/(total PSA). Furthermore, they could associate the SNP rs10993994 to elevated PCa risk, elevated total PSA value, elevated free PSA value and elevated hk2 value, and finally SNP rs198977 was associated with elevated PCa risk, elevated value of (free PSA)/(total PSA), and elevated hk2 value.

In practice, one common method for associating a SNP with a condition relies on access to a case-control clinical trial which compares two large groups of individuals, one healthy control group and one case group having the condition under study. All the individuals in each group are genotyped for the majority of common known SNPs. When all genotyping data is available, it is investigated if the allele frequency is significantly altered between the case group and the control group. In such setups, the typical unit for reporting effect sizes is the odds ratio. The odds ratio reports the ratio between two proportions: the proportion of individuals in the case group having a specific allele, and the proportions of individuals in the control group having the same allele. If the allele frequency in the case group is significantly higher than the allele frequency in the control group, the odds ratio will be higher than 1. If the allele frequency in the case group is significantly lower than the allele frequency in the control group, the odds ratio will be smaller than 1.

One preferred method for combining information from multiple sources has been described in the public report "Polygenic Risk Score Improves Prostate Cancer Risk Prediction: Results from the Stockholm-1 Cohort Study" by Markus Aly and co-authors as published in EUROPEAN UROLOGY 60 (2011) 21-28 (which is incorporated by reference herein). Associations between each SNP and PCa at biopsy were assessed using a Cochran-Armitage trend test. Allelic odds ratios (OR) with 95% confidence intervals were computed using logistic regression models. For each patient, a genetic risk score was created by summing up the number of risk alleles (0, 1, or 2) at each of the SNPs multiplied by the logarithm of that SNP's OR. Associations between PCa diagnosis and evaluated risk factors were explored in logistic regression analysis. The portion of the model related to non-genetic information included logarithmically transformed total PSA, the logarithmically transformed free-to-total PSA ratio, age at biopsy, and family history of PCa (yes or no). A repeated 10-fold cross-validation was used to estimate the predicted probabilities of PCa at biopsy. Ninety-five percent confidence intervals for the ROC-AUC values were constructed using a normal approximation. All reported p values are based on two-sided hypotheses. Even though the method of Aly and co-authors are described in the context of PCa screening, the same approach can be applied for prognostic methods.

In most cases, prostate cancer is a slowly progressing disease. Thus, the ability to recommend an individual to go through active therapy, already prior to biopsy, makes it possible for example to motivate the individual to change life-style in preparation for active therapy, should that be necessary. To stop smoking, to reach a BMI value below 30 and to exercise regularly (approximately 30 minutes 3-6 days of the week) are all factors that in general promotes survival in conditions of severe disease, including prostate cancer. Hence, if an individual is found suitable for active therapy it is reason to suggest to said individual to stop smoking, try to reach BMI<30 and start exercising so as to better withstand the side effects of therapy a such and to increase the chances of recovering from the disease. Another important aspect is dietary issues. Through changing the diet, the PCa development may be reduced or delayed. There is evidence suggesting that reduced dairy intake can reduce the risk for onset of PCa as reported by Song and co-authors in the publication "Whole milk intake is associated with prostate cancer-specific mortality among U.S. male physicians." as published in J Nutr. 2013 February; 143(2):189-96 (which is incorporated by reference herein). Similar evidence exists for the positive effects of intake of green tea and intake of soy products. Hence, if an individual is found suitable for active therapy it is reason to suggest to said individual to decrease intake of dairy products and/or increase intake of green tea and soy based products to delay or even prevent going through active therapy.

Example 1

To illustrate the current invention, a data set comprising 172 cases (subjects known to suffer from PCa that received active treatment) and 79 controls (subjects known to suffer from PCa where watchful waiting was decided) from the STHLM2 data set was extracted. The STHLM2 data set has been discussed in the public domain as evident on the web-page http://sthlm2.se/. In summary, during 2010-2012 about 26000 men who did a PSA test in the Stockholm area were included in the STHLM2 study. The 172+79=251 subjects were characterized with respect to the following biomarkers and SNPs:

Biomarkers:
Total prostate-specific antigen (tPSA) [ng/mL]
Intact prostate-specific antigen (iPSA) [ng/mL]
Free prostate-specific antigen (fPSA) [ng/mL]
human kallikrein 2 (hK2) [ng/mL]
Macrophage Inhibitory Cytokine 1 (MIC-1) [ng/mL]
beta-microseminoprotein (MSMB) [ng/mL]
SNPs:
657del5, rs10086908, rs1016343, rs10187424, rs1041449, rs10486567, rs1054564, rs10875943, rs10896449, rs10934853, rs10993994, rs11067228, rs11135910, rs11228565, rs11568818, rs11649743, rs11650494, rs11672691, rs11704416, rs12130132, rs12409639, rs12418451, rs12500426, rs12543663, rs12621278, rs12653946, rs1270884, rs130067, rs13252298, rs13385191, rs1354774, rs1363120, rs137853007, rs138213197, rs1447295, rs1465618, rs1512268, rs1571801, rs16901979, rs16902094, rs17021918, rs17632542, rs17879961, rs1859962, rs1894292, rs1933488, rs1983891, rs2018334, rs2121875, rs2242652, rs2273669, rs2292884, rs2405942, rs2660753, rs2735839, rs2736098, rs2928679, rs3213764, rs339331, rs3771570, rs3850699, rs3863641, rs401681, rs4245739, rs4430796, rs445114, rs4643253, rs4857841, rs4962416, rs5759167, rs5919432, rs5945619, rs6062509, rs620861, rs6465657, rs6763931, rs684232, rs6869841, rs6983267, rs6983561, rs7127900, rs7210100, rs721048, rs7241993, rs7611694, rs7679673, rs7931342, rs8008270, rs8102476, rs888663, rs902774, rs9364554, rs9600079, rs9623117

Background information for each subject was collected, including age and family history (yes or no). Age was expressed in the units of years.

In order to forecast which subjects that should be recommended active therapy, it was possible to rely on the genetic score alone, as illustrated in the following pre-determined equation:

$$y=0.63+0.039*score$$

In this equation, 'score' is here the genetic score variable computed as described in the public report "Polygenic Risk Score Improves Prostate Cancer Risk Prediction: Results from the Stockholm-1 Cohort Study" by Markus Aly and co-authors as published in EUROPEAN UROLOGY 60 (2011) 21-28 (which is incorporated by reference herein) containing the validated prostate cancer susceptibility SNPs (said SNP being related to prostate cancer susceptibility or related to PSA, free-PSA, MSMB and MIC-1 biomarker plasma levels) listed in the present example.

The resulting value 'y' will be strongly correlated with the need for active therapy, as illustrated in FIG. 1. The ROC curves in FIG. 1 represent forecasting the need for active therapy using PSA value (101; solid line) alone and the model described in this example (102; dashed line). If y is above a cutoff value the man should be recommended a referral to a urologist for examination of the prostate using biopsies.

The value of the cutoff depends on the tradeoff between test sensitivity and specificity. If, for example, the cut off value of 1.04 is used, this particular test will result in test sensitivity of 0.5 and specificity of 0.67. This can be compared to using the PSA value alone as a screening test, which results in a sensitivity of 0.5 and specificity of 0.46. It is important to note that for this particular prognostic method, the most valuable performance is to support the decision for individuals in the grey-zone, i.e. at sensitivity level 0.5-0.6.

Example 2

To illustrate the current invention further, the data set as described in Example 1 was subjected to additional analysis. By combining information from several categories, including genetic score and biomarker concentrations, a multiparametric model including the above biomarkers and the genetic score as described in Example 1. The model was derived using linear regression.

Figure 2:
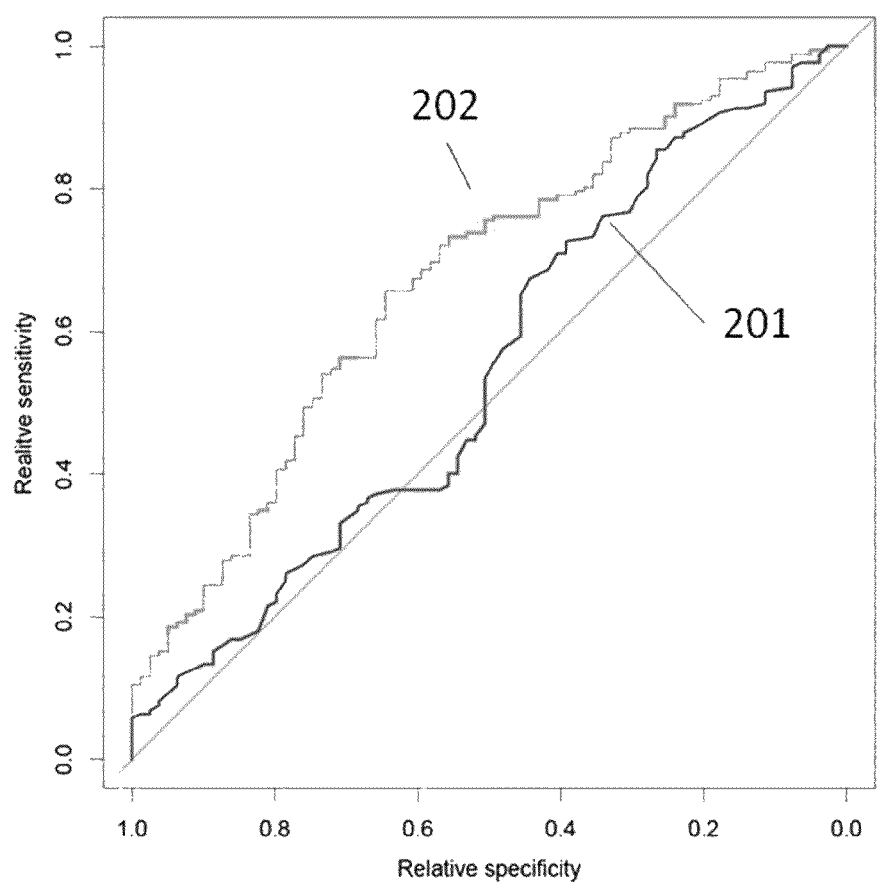
FIG. 2 shows the ROC curves for the linear model of Example 1 illustrating the difference in performance between PSA (201) and a multiparametric model (202) in prediction if active treatment is required.

The resulting value 'y' of this model will be strongly correlated with the need for active therapy, as illustrated in FIG. 2. The ROC curves in FIG. 2 represent forecasting the need for active therapy using PSA value (201) alone and the model described in this example (202). If y is above a cutoff value the man should be recommended a referral to a urologist for examination of the prostate using biopsies.

The value of the cutoff depends on the tradeoff between test sensitivity and specificity. If, for example, the cut off value of 0.72 is used, this particular test will result in test sensitivity of 0.5 and specificity of 0.78. This can be compared to using the PSA value alone as a screening test, which results in a sensitivity of 0.5 and specificity of 0.46. It is important to note that for this particular prognostic method, the most valuable performance is to support the decision for individuals in the grey-zone, i.e. at sensitivity level 0.5-0.6.

Example 3

To illustrate the current invention even further, a subset of the data set of Example 1 was extracted by omitting all individuals with PSA>7 ng/mL, or in the case a PSA value was missing individuals with free PSA>0.91 ng/mL were omitted.

The subset contained 144 individuals. Four different models were derived in an attempt to predict if the individual received active treatment.

$Y1=1.4076640+0.0352188*PSA-0.0159339*Age-0.0005042*PSA*Age$ $Y2=6.420955-0.897462*score-0.445241*PSA-0.067727*Age+0.081441*score*PSA+0.009316*score*Age+0.000848*PSA*Age$ $Y3=3.901443-0.408785*score90-0.262197*PSA-0.040232*Age+0.045336*score90*PSA+0.003840*score90*Age+0.001104*PSA*Age$ $Y4=3.503319-0.337091*score-2.747459*fPSA-0.042007*Age+1.243013*intact+0.242149*score*fPSA-0.070408*score*intact+0.019290*fPSA*Age+0.205893*fPSA*intact-0.014322*Age*intact$ Where PSA is the concentration PSA, fPSA the concentration of free PSA, intact the concentration of intact PSA, Age the age of the individual, score the genetic score, and score90 the genetic score calculated using only 90% (randomly selected) of the SNP. The model Y1 had a ROC-AUC=0.60, the model Y2 had a ROC-AUC=0.69, Y3 had a ROC-AUC=0.65 and Y4 had a ROC-AUC=0.68.

This example illustrates four different aspects of the invention:

A first aspect is the ability to predict if a patient did receive active treatment benefits from the inclusion of genetic score (seen in the comparison of models Y1 and Y2).

A second aspect is that the model Y2 has inherent redundancy in the score parameter and will have good performance for model Y3 in comparison to the model Y1 (which does not use any genetic information) even though 10% of the SNP information is missing in Y3. Missing data can occur due to a multitude of reasons, such as technical problems, lack of sample material or human error to mention some non-limiting examples.

A third aspect is that the PSA protein biomarker (which belongs to the kallikrein-like biomarker family) can be substituted with other members of the kallikrein biomarker family (illustrated in model Y4) with preserved good performance as compared to the simpler model Y1. Note that the inclusion criterion for individuals lacking information about PSA value is free PSA<0.91.

A fourth aspect is that this example illustrates that it is possible to provide information for the category of individuals where the decision if and how to treat is difficult to make. Whereas individuals with high PSA value (larger than 7 ng/mL, or even larger than 30 ng/mL) usually are candidates for active therapy, individuals with lower PSA value are within a greyzone where risk to benefit ratios are not always easily determined Although the invention has been described with regard to its preferred embodiment, which constitutes the best mode currently known to the inventor, it should be understood that various changes and modifications as would be obvious to one having ordinary skill in this art may be made without departing from the scope of the invention as set forth in the claims appended hereto.

The invention claimed is:

1. A method for determining PCa markers in an individual, comprising the steps of:
    (i) Providing at least one biological sample from said individual;
    (ii) Contacting the biological sample with an assay device comprising a solid phase having immobilised thereon a first category of ligands which bind specifically to at least 80 SNPs related to PCa (SNPpc), the first category of ligands including a plurality of different ligands binding specifically to each of said SNPpc, wherein
        (a) the at least 80 SNPpc are selected from the group consisting of 657del5, rs10086908, rs1016343, rs10187424, rs1041449, rs10486567, rs1054564, rs10875943, rs10896449, rs10934853, rs10993994, rs11067228, rs11135910, rs11228565, rs11568818, rs11649743, rs11650494, rs11672691, rs11704416, rs12130132, rs12409639, rs12418451, rs12500426, rs12543663, rs12621278, rs12653946, rs1270884, rs130067, rs13252298, rs13385191, rs1354774, rs1363120, rs137853007, rs138213197, rs1447295, rs1465618, rs1512268, rs1571801, rs16901979, rs16902094, rs17021918, rs17632542, rs17879961, rs1859962, rs1894292, rs1933488, rs1983891, rs2018334, rs2121875, rs2242652, rs2273669, rs2292884, rs2405942, rs2660753, rs2735839, rs2736098, rs2928679, rs3213764, rs339331, rs3771570, rs3850699, rs3863641, rs401681, rs4245739, rs4430796, rs445114, rs4643253, rs4857841, rs4962416, rs5759167, rs5919432, rs5945619, rs6062509, rs620861, rs6465657, rs6763931, rs684232, rs6869841, rs6983267, rs6983561, rs7127900, rs7210100, rs721048, rs7241993, rs7611694, rs7679673, rs7931342, rs8008270, rs8102476, rs888663, rs902774, rs9364554, rs9600079, and rs9623117; or
        (b) the at least 80 SNPpc are selected from the group consisting of rs582598, rs439378, rs2207790, rs1046011, rs10458360, rs7525167, rs10489871, rs7529518, rs4245739, rs4512641, rs10178804, rs11900952, rs1873555, rs10191478, rs6755901, rs6545962, rs721048, rs2710647, rs12612891, rs2028900, rs1009, rs12233245, rs6760417, rs10496470, rs10199796, rs12475433, rs16860513, rs12151618, rs3765065, rs13017302, rs12988652, rs871688, rs749264, rs3771570, rs4346531, rs6770955, rs12637074, rs2660753, rs13319878, rs6437715, rs2162185, rs1515542, rs2270785, rs9830294, rs1439024, rs6762443, rs888507, rs6794467, rs12490248, rs1477886, rs4833103, rs3796547, rs17779822, rs2366711, rs16849146, rs1894292, rs12640320, rs3805284, rs12500426, rs4699312, rs17021918, rs7679673, rs2047408, rs2647262, rs12506850, rs7658048, rs2078277, rs12505546, rs13113975, rs4246742, rs2736098, rs401681, rs11134144, rs10060513, rs40485, rs2087724, rs1482679, rs16901841, rs1295683, rs2070874, rs7752029, rs2018334, rs9358913, rs1140809, rs409558, rs3096702, rs9267911, rs2025645, rs9359428, rs6569371, rs2813532, rs1933488, rs712242, rs6934898, rs9456490, rs651164, rs3120137, rs9364554, rs9457937, rs10486562, rs10807843, rs7801918, rs6962297, rs2465796, rs6957416, rs7777631, rs2272316, rs6961773, rs2132276, rs13265330, rs16887736, rs2911756, rs2272668, rs2339654, rs1380862, rs9297746, rs12543663, rs10086908, rs16901922, rs1016343, rs17832285, rs16901979, rs4871779, rs10107982, rs16902094, rs620861, rs17467139, rs6983267, rs9297756, rs10094059, rs7818556, rs1992833, rs986472, rs12552397, rs4273907, rs4237185, rs753032, rs11253002, rs2386841, rs10795841, rs10508422, rs7075945, rs10508678, rs539357, rs10826398, rs3818714, rs7090755, rs10993994, rs4382847, rs1891158, rs10887926, rs10788160, rs6579002, rs10832514, rs7358335, rs1944047, rs3019779, rs10896437, rs12793759, rs7106762, rs7102758, rs2449600, rs585197, rs2509867, rs11568818, rs7125415, rs11601037, rs11222496, rs4570588, rs6489721, rs3213764, rs17395631, rs4423250, rs11168936, rs10875943, rs3759129, rs902774, rs1827611, rs4760442, rs11610799, rs6539333, rs11067228, rs7485441, rs6489794, rs4119478, rs17070292, rs2293710, rs17256058, rs1950198, rs2331780, rs7141529, rs12880777, rs17123359, rs785437, rs524908, rs12903579, rs7178085, rs7164364, rs896615, rs11634741, rs9972541, rs12594014, rs11631109, rs1558902, rs8044335, rs2738571, rs885479, rs385894, rs684232, rs4925094, rs17138478, rs11649743, rs2107131, rs7213769, rs12946864, rs306801, rs138213197, rs1863610, rs17224342, rs9911515, rs12947919, rs966304, rs17744022, rs7234917, rs1943821, rs2227270, rs1363120, rs888663, rs1227732, rs1054564, rs4806120, rs11672691, rs758643, rs3745233, rs6509345, rs2659051, rs2735839, rs1354774, rs2691274, rs6090461, rs2297434, rs6062509, rs2315654, rs2823118, rs2838053, rs398146, rs16988279, rs2269640, rs4822763, rs132774, rs747745, rs5978944, rs6530238, rs5934705, rs5935063, rs4830488, rs17318620, rs5945619, rs5945637, rs11091768, rs2473057, rs5918762, rs4844228, rs6625760 and rs17324573;

(iii) In said biological sample, measuring a presence or absence of each of the at least 80 SNPpc binding the ligands in the first category; and (iv) Combining measurement data of the at least 80 SNPpc binding ligands from said first category of ligands from step (iii) according to a first predetermined equation to form a SNPpc composite value, wherein the combination according to the first predetermined equation allows omission of measurement data of a subset of at least about 10% of the SNPpc of the SNPpc category when forming the SNPpc composite value.

2. The method of claim 1, wherein the SNPpc are selected from the group consisting of: 657del5, rs10086908, rs1016343, rs10187424, rs1041449, rs10486567, rs1054564, rs10875943, rs10896449, rs10934853, rs10993994, rs11067228, rs11135910, rs11228565, rs11568818, rs11649743, rs11650494, rs11672691, rs11704416, rs12130132, rs12409639, rs12418451, rs12500426, rs12543663, rs12621278, rs12653946, rs1270884, rs130067, rs13252298, rs13385191, rs1354774, rs1363120, rs137853007, rs138213197, rs1447295, rs1465618, rs1512268, rs1571801, rs16901979, rs16902094, rs17021918, rs17632542, rs17879961, rs1859962, rs1894292, rs1933488, rs1983891, rs2018334, rs2121875, rs2242652, rs2273669, rs2292884, rs2405942, rs2660753, rs2735839, rs2736098, rs2928679, rs3213764, rs339331, rs3771570, rs3850699, rs3863641, rs401681, rs4245739, rs4430796, rs445114, rs4643253, rs4857841, rs4962416, rs5759167, rs5919432, rs5945619, rs6062509, rs620861, rs6465657, rs6763931, rs684232, rs6869841, rs6983267, rs6983561, rs7127900, rs7210100, rs721048, rs7241993, rs7611694, rs7679673, rs7931342, rs8008270, rs8102476, rs888663, rs902774, rs9364554, rs9600079, and rs9623117.

3. The method of claim 1, further comprising contacting the biological sample with an assay device comprising a second category of ligands which bind specifically to each of a plurality of PCa biomarkers; measuring a presence or concentration of each of the plurality of PCa biomarkers binding the ligands in the second category; combining measurement data of the PCa biomarkers according to a second predetermined equation to form a biomarker composite value; and combining the biomarker composite value and the SNPpc composite value according to a third predetermined equation to form an overall composite value.

4. The method of claim 3, wherein the plurality of PCa biomarkers include at least partially redundant PCa biomarkers, and wherein at least one of the PCa biomarkers is selected from the group consisting of (i) PSA, (ii) total PSA (tPSA), (iii) intact PSA (iPSA), (iv) free PSA (fPSA), and (v) hK2.

5. The method of claim 4, wherein the combination according to the second predetermined equation allows omission of measurement data of a subset of at least one of said PCa biomarkers (i)-(v) of the plurality of PCa biomarkers when forming said biomarker composite value.

6. The method of claim 3, further comprising contacting the biological sample with an assay device comprising a third category of ligands which bind specifically to at least one additional PCa biomarker, the third category of ligands including a plurality of different ligands binding specifically to each of the additional PCa biomarkers; measuring the presence or concentration of each of said at least one additional PCa biomarker; combining measurement data regarding said at least one additional PCa biomarker according to a fourth predetermined equation to form an additional biomarker composite value for said at least one additional PCa biomarker; and combining said additional biomarker composite value with the biomarker composite value and the SNPpc composite value according to the third predetermined equation to form the overall composite value; wherein the combination of measurement data to form the additional biomarker composite value allows omission of measurement data of at least one of the members of the at least one additional PCa biomarker where the at least one additional PCa biomarker comprises more than one PCa biomarker.

7. The method of claim 6, wherein the at least one additional PCa biomarker comprises the biomarker MIC-1.

8. The method of claim 3, wherein combining the measurement data of said PCa biomarkers according to the second predetermined equation comprises calculating a weighted average value of the measurement data of said PCa biomarkers based on the importance of the respective PCa biomarkers in a determination of PCa.

9. The method of claim 3, wherein the third predetermined equation comprises a linear equation or a non-linear polynomial equation based on a group of individuals having PCa and a group of individuals not having PCa.

10. The method of claim 1, wherein the measuring step employs a category of detection molecules which is capable of detecting each of the at least 80 SNPpc, and wherein the at least 80 SNPpc are selected from the group consisting of rs582598, rs439378, rs2207790, rs1046011, rs10458360, rs7525167, rs10489871, rs7529518, rs4245739, rs4512641, rs10178804, rs11900952, rs1873555, rs10191478, rs6755901, rs6545962, rs721048, rs2710647, rs12612891, rs2028900, rs1009, rs12233245, rs6760417, rs10496470, rs10199796, rs12475433, rs16860513, rs12151618, rs3765065, rs13017302, rs12988652, rs871688, rs749264, rs3771570, rs4346531, rs6770955, rs12637074, rs2660753, rs13319878, rs6437715, rs2162185, rs1515542, rs2270785, rs9830294, rs1439024, rs6762443, rs888507, rs6794467, rs12490248, rs1477886, rs4833103, rs3796547, rs17779822, rs2366711, rs16849146, rs1894292, rs12640320, rs3805284, rs12500426, rs4699312, rs17021918, rs7679673, rs2047408, rs2647262, rs12506850, rs7658048, rs2078277, rs12505546, rs13113975, rs4246742, rs2736098, rs401681, rs11134144, rs10060513, rs40485, rs2087724, rs1482679, rs16901841, rs1295683, rs2070874, rs7752029, rs2018334, rs9358913, rs1140809, rs409558, rs3096702, rs9267911, rs2025645, rs9359428, rs6569371, rs2813532, rs1933488, rs712242, rs6934898, rs9456490, rs651164, rs3120137, rs9364554, rs9457937, rs10486562, rs10807843, rs7801918, rs6962297, rs2465796, rs6957416, rs7777631, rs2272316, rs6961773, rs2132276, rs13265330, rs16887736, rs2911756, rs2272668, rs2339654, rs1380862, rs9297746, rs12543663, rs10086908, rs16901922, rs1016343, rs17832285, rs16901979, rs4871779, rs10107982, rs16902094, rs620861, rs17467139, rs6983267, rs9297756, rs10094059, rs7818556, rs1992833, rs986472, rs12552397, rs4273907, rs4237185, rs753032, rs11253002, rs2386841, rs10795841, rs10508422, rs7075945, rs10508678, rs539357, rs10826398, rs3818714, rs7090755, rs10993994, rs4382847, rs1891158, rs10887926, rs10788160, rs6579002, rs10832514, rs7358335, rs1944047, rs3019779, rs10896437, rs12793759, rs7106762, rs7102758, rs2449600, rs585197, rs2509867, rs11568818, rs7125415, rs11601037, rs11222496, rs4570588, rs6489721, rs3213764, rs17395631, rs4423250, rs11168936, rs10875943, rs3759129, rs902774, rs1827611, rs4760442, rs11610799, rs6539333, rs11067228, rs7485441, rs6489794, rs4119478, rs17070292, rs2293710, rs17256058, rs1950198, rs2331780, rs7141529, rs12880777, rs17123359, rs785437, rs524908, rs12903579, rs7178085, rs7164364, rs896615, rs11634741, rs9972541, rs12594014, rs11631109, rs1558902, rs8044335, rs2738571, rs885479, rs385894, rs684232, rs4925094, rs17138478, rs11649743, rs2107131, rs7213769, rs12946864, rs306801, rs138213197, rs1863610, rs17224342, rs9911515, rs12947919, rs966304, rs17744022, rs7234917, rs1943821, rs2227270, rs1363120, rs888663, rs1227732, rs1054564, rs4806120, rs11672691, rs758643, rs3745233, rs6509345, rs2659051, rs2735839, rs1354774, rs2691274, rs6090461, rs2297434, rs6062509, rs2315654, rs2823118, rs2838053, rs398146, rs16988279, rs2269640, rs4822763, rs132774, rs747745, rs5978944, rs6530238, rs5934705, rs5935063, rs4830488, rs17318620, rs5945619, rs5945637, rs11091768, rs2473057, rs5918762, rs4844228, rs6625760 and rs17324573.

11. The method of claim 1, further comprising collecting family history regarding PCa, treatment history, and physical data from said individual; and wherein said family history, treatment history and/or physical data are combined with the SNPpc composite value according to a predetermined equation to form an overall composite value.

12. The method of claim 1, wherein said biological sample is a blood sample.

13. The method of claim 1, wherein the assay device comprising a solid phase is a microarray.

14. The method of claim 1, wherein the measuring step employs a category of detection molecules which is capable of detecting each of the at least 80 SNPpc, and wherein said at least 80 SNPpc are selected from the group consisting of 657del5, rs10086908, rs1016343, rs10187424, rs1041449, rs10486567, rs1054564, rs10875943, rs10896449, rs10934853, rs10993994, rs11067228, rs11135910, rs11228565, rs11568818, rs11649743, rs11650494, rs11672691, rs11704416, rs12130132, rs12409639, rs12418451, rs12500426, rs12543663, rs12621278, rs12653946, rs1270884, rs130067, rs13252298, rs13385191, rs1354774, rs1363120, rs137853007, rs138213197, rs1447295, rs1465618, rs1512268, rs1571801, rs16901979, rs16902094, rs17021918, rs17632542, rs17879961, rs1859962, rs1894292, rs1933488, rs1983891, rs2018334, rs2121875, rs2242652, rs2273669, rs2292884, rs2405942, rs2660753, rs2735839, rs2736098, rs2928679, rs3213764, rs339331, rs3771570, rs3850699, rs3863641, rs401681, rs4245739, rs4430796, rs445114, rs4643253, rs4857841, rs4962416, rs5759167, rs5919432, rs5945619, rs6062509, rs620861, rs6465657, rs6763931, rs684232, rs6869841, rs6983267, rs6983561, rs7127900, rs7210100, rs721048, rs7241993, rs7611694, rs7679673, rs7931342, rs8008270, rs8102476, rs888663, rs902774, rs9364554, rs9600079, and rs9623117.

15. The method of claim 1, wherein step (iv) is executed in a computer comprising a processor and memory.

16. The method of claim 1, wherein step (iv) is conducted with a computer programmed to form or calculate a SNPpc composite value from the data of step (iii).

17. The method of claim 1, wherein combining the measurement data of said category of SNPpc according to the first predetermined equation comprises calculating an average value of an odds ratio of each individual SNPpc included in said category of SNPpc, wherein the odds ratio of an individual SNPpc is based on the likelihood that an individual who carries the individual SNPpc has PCa.

18. The method of claim 1, wherein the at least 80 SNPpc are selected from the group consisting of rs582598, rs439378, rs2207790, rs1046011, rs10458360, rs7525167, rs10489871, rs7529518, rs4245739, rs4512641, rs10178804, rs11900952, rs1873555, rs10191478, rs6755901, rs6545962, rs721048, rs2710647, rs12612891, rs2028900, rs1009, rs12233245, rs6760417, rs10496470, rs10199796, rs12475433, rs16860513, rs12151618, rs3765065, rs13017302, rs12988652, rs871688, rs749264, rs3771570, rs4346531, rs6770955, rs12637074, rs2660753, rs13319878, rs6437715, rs2162185, rs1515542, rs2270785, rs9830294, rs1439024, rs6762443, rs888507, rs6794467, rs12490248, rs1477886, rs4833103, rs3796547, rs17779822, rs2366711, rs16849146, rs1894292, rs12640320, rs3805284, rs12500426, rs4699312, rs17021918, rs7679673, rs2047408, rs2647262, rs12506850, rs7658048, rs2078277, rs12505546, rs13113975, rs4246742, rs2736098, rs401681, rs11134144, rs10060513, rs40485, rs2087724, rs1482679, rs16901841, rs1295683, rs2070874, rs7752029, rs2018334, rs9358913, rs11140809, rs409558, rs3096702, rs9267911, rs2025645, rs9359428, rs6569371, rs2813532, rs1933488, rs712242, rs6934898, rs9456490, rs651164, rs3120137, rs9364554, rs9457937, rs10486562, rs10807843, rs7801918, rs6962297, rs2465796, rs6957416, rs7777631, rs2272316, rs6961773, rs2132276, rs13265330, rs16887736, rs2911756, rs2272668, rs2339654, rs1380862, rs9297746, rs12543663, rs10086908, rs16901922, rs1016343, rs17832285, rs16901979, rs4871779, rs10107982, rs16902094, rs620861, rs17467139, rs6983267, rs9297756, rs10094059, rs7818556, rs1992833, rs986472, rs12552397, rs4273907, rs4237185, rs753032, rs11253002, rs2386841, rs10795841, rs10508422, rs7075945, rs10508678, rs539357, rs10826398, rs3818714, rs7090755, rs10993994, rs4382847, rs1891158, rs10887926, rs10788160, rs6579002, rs10832514, rs7358335, rs1944047, rs3019779, rs10896437, rs12793759, rs7106762, rs7102758, rs2449600, rs585197, rs2509867, rs11568818, rs7125415, rs11601037, rs11222496, rs4570588, rs6489721, rs3213764, rs17395631, rs4423250, rs11168936, rs10875943, rs3759129, rs902774, rs1827611, rs4760442, rs11610799, rs6539333, rs11067228, rs7485441, rs6489794, rs4119478, rs17070292, rs2293710, rs17256058, rs1950198, rs2331780, rs7141529, rs12880777, rs17123359, rs785437, rs524908, rs12903579, rs7178085, rs7164364, rs896615, rs11634741, rs9972541, rs12594014, rs11631109, rs1558902, rs8044335, rs2738571, rs885479, rs385894, rs684232, rs4925094, rs17138478, rs11649743, rs2107131, rs7213769, rs12946864, rs306801, rs138213197, rs1863610, rs17224342, rs9911515, rs12947919, rs966304, rs17744022, rs7234917, rs1943821, rs2227270, rs1363120, rs888663, rs1227732, rs1054564, rs4806120, rs11672691, rs758643, rs3745233, rs6509345, rs2659051, rs2735839, rs1354774, rs2691274, rs6090461, rs2297434, rs6062509, rs2315654, rs2823118, rs2838053, rs398146, rs16988279, rs2269640, rs4822763, rs132774, rs747745, rs5978944, rs6530238, rs5934705, rs5935063, rs4830488, rs17318620, rs5945619, rs5945637, rs11091768, rs2473057, rs5918762, rs4844228, rs6625760 and rs17324573.

19. A method for determining PCa markers in an individual, comprising the steps of:
(i) Providing at least one biological sample from said individual;

(ii) Contacting the biological sample with an assay device comprising a solid phase having immobilised thereon a first category of ligands which bind specifically to at least 80 SNPs related to PCa (SNPpc), the second category of ligands including a plurality of different ligands binding specifically to each of said SNPpc, wherein (a) the at least 80 SNPpc are selected from the group consisting of 657del5, rs10086908, rs1016343, rs10187424, rs1041449, rs10486567, rs1054564, rs10875943, rs10896449, rs10934853, rs10993994, rs11067228, rs11135910, rs11228565, rs11568818, rs11649743, rs11650494, rs11672691, rs11704416, rs12130132, rs12409639, rs12418451, rs12500426, rs12543663, rs12621278, rs12653946, rs1270884, rs130067, rs13252298, rs13385191, rs1354774, rs1363120, rs137853007, rs138213197, rs1447295, rs1465618, rs1512268, rs1571801, rs16901979, rs16902094, rs17021918, rs17632542, rs17879961, rs1859962, rs1894292, rs1933488, rs1983891, rs2018334, rs2121875, rs2242652, rs2273669, rs2292884, rs2405942, rs2660753, rs2735839, rs2736098, rs2928679, rs3213764, rs339331, rs3771570, rs3850699, rs3863641, rs401681, rs4245739, rs4430796, rs445114, rs4643253, rs4857841, rs4962416, rs5759167, rs5919432, rs5945619, rs6062509, rs620861, rs6465657, rs6763931, rs684232, rs6869841, rs6983267, rs6983561, rs7127900, rs7210100, rs721048, rs7241993, rs7611694, rs7679673, rs7931342, rs8008270, rs8102476, rs888663, rs902774, rs9364554, rs9600079, and rs9623117; or (b) the at least 80 SNPpc are selected from the group consisting of rs582598, rs439378, rs2207790, rs1046011, rs10458360, rs7525167, rs10489871, rs7529518, rs4245739, rs4512641, r510178804, rs11900952, rs1873555, rs10191478, rs6755901, rs6545962, rs721048, rs2710647, rs12612891, rs2028900, rs1009, rs12233245, rs6760417, rs10496470, rs10199796, rs12475433, rs16860513, rs12151618, rs3765065, rs13017302, rs12988652, rs871688, rs749264, rs3771570, rs4346531, rs6770955, rs12637074, rs2660753, rs13319878, rs6437715, rs2162185, rs1515542, rs2270785, rs9830294, rs1439024, rs6762443, rs888507, rs6794467, rs12490248, rs1477886, rs4833103, rs3796547, rs17779822, rs2366711, rs16849146, rs1894292, rs12640320, rs3805284, rs12500426, rs4699312, rs17021918, rs7679673, rs2047408, rs2647262, rs12506850, rs7658048, rs2078277, rs12505546, rs13113975, rs4246742, rs2736098, rs401681, rs11134144, rs10060513, rs40485, rs2087724, rs1482679, rs16901841, rs1295683, rs2070874, rs7752029, rs2018334, rs9358913, rs1140809, rs409558, rs3096702, rs9267911, rs2025645, rs9359428, rs6569371, rs2813532, rs1933488, rs712242, rs6934898, rs9456490, rs651164, rs3120137, rs9364554, rs9457937, rs10486562, rs10807843, rs7801918, rs6962297, rs2465796, rs6957416, rs7777631, rs2272316, rs6961773, rs2132276, rs13265330, rs16887736, rs2911756, rs2272668, rs2339654, rs1380862, rs9297746, rs12543663, rs10086908, rs16901922, rs1016343, rs17832285, rs16901979, rs4871779, rs10107982, rs16902094, rs620861, rs17467139, rs6983267, rs9297756, rs10094059, rs7818556, rs1992833, rs986472, rs12552397, rs4273907, rs4237185, rs753032, rs11253002, rs2386841, rs10795841, rs10508422, rs7075945, rs10508678, rs539357, rs10826398, rs3818714, rs7090755, rs10993994, rs4382847, rs1891158, rs10887926, rs10788160, rs6579002, rs10832514, rs7358335, rs1944047, rs3019779, rs10896437, rs12793759, rs7106762, rs7102758, rs2449600, rs585197, rs2509867, rs11568818, rs7125415, rs11601037, rs11222496, rs4570588, rs6489721, rs3213764, rs17395631, rs4423250, rs11168936, rs10875943, rs3759129, rs902774, rs1827611, rs4760442, rs11610799, rs6539333, rs11067228, rs7485441, rs6489794, rs4119478, rs17070292, rs2293710, rs17256058, rs1950198, rs2331780, rs7141529, rs12880777, rs17123359, rs785437, rs524908, rs12903579, rs7178085, rs7164364, rs896615, rs11634741, rs9972541, rs12594014, rs11631109, rs1558902, rs8044335, rs2738571, rs885479, rs385894, rs684232, rs4925094, rs17138478, rs11649743, rs2107131, rs7213769, rs12946864, rs306801, rs138213197, rs1863610, rs17224342, rs9911515, rs12947919, rs966304, rs17744022, rs7234917, rs1943821, rs2227270, rs1363120, rs888663, rs1227732, rs1054564, rs4806120, rs11672691, rs758643, rs3745233, rs6509345, rs2659051, rs2735839, rs1354774, rs2691274, rs6090461, rs2297434, rs6062509, rs2315654, rs2823118, rs2838053, rs398146, rs16988279, rs2269640, rs4822763, rs132774, rs747745, rs5978944, rs6530238, rs5934705, rs5935063, rs4830488, rs17318620, rs5945619, rs5945637, rs11091768, rs2473057, rs5918762, rs4844228, rs6625760 and rs17324573; and (iii) In said biological sample, measuring a presence or absence of each of the at least 80 SNPpc binding the ligands in the first category.

* * * * *

UNITED STATES PATENT AND TRADEMARK OFFICE
CERTIFICATE OF CORRECTION

PATENT NO. : 10,428,385 B2
APPLICATION NO. : 14/443974
DATED : October 1, 2019
INVENTOR(S) : Henrik Grönberg et al.

Page 1 of 1

It is certified that error appears in the above-identified patent and that said Letters Patent is hereby corrected as shown below:

On the Title Page

Item (30):
Change "1251310" to --1251310-7--.
Change "1350602" to --1350602-7--.

In the Claims

Claim 19, Column 31, Line 36, change "r510178804" to --rs10178804--.

Signed and Sealed this
Seventh Day of January, 2020

Andrei Iancu
*Director of the United States Patent and Trademark Office*